United States Patent
Goldman et al.

(10) Patent No.: US 6,812,027 B2
(45) Date of Patent: Nov. 2, 2004

(54) DISCOVERY, LOCALIZATION, HARVEST, AND PROPAGATION OF AN FGF2 AND BDNF-RESPONSIVE POPULATION OF NEURAL AND NEURONAL PROGENITOR CELLS IN THE ADULT HUMAN FOREBRAIN

(75) Inventors: Steven A. Goldman, South Salem, NY (US); Maiken Nedergaard, South Salem, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 82 days.

(21) Appl. No.: 09/271,969

(22) Filed: Mar. 18, 1999

(65) Prior Publication Data

US 2003/0049234 A1 Mar. 13, 2003

Related U.S. Application Data

(60) Provisional application No. 60/079,226, filed on Mar. 25, 1998.

(51) Int. Cl.[7] .............................. C12N 5/00; C12N 5/02; C12N 5/08; C12N 15/63; C12N 33/563
(52) U.S. Cl. ....................... 435/377; 435/325; 435/366; 435/368; 435/383; 435/384; 435/455; 436/513
(58) Field of Search ................................. 435/325, 366, 435/368, 377, 383, 384, 455; 436/513

(56) References Cited

U.S. PATENT DOCUMENTS

| | | | |
|---|---|---|---|
| 5,750,376 A | * 5/1998 | Weiss et al. | 435/69.52 |
| 5,753,505 A | * 5/1998 | Luskin | 435/375 |
| 5,851,832 A | * 12/1998 | Weiss et al. | 435/368 |
| 6,245,564 B1 | 6/2001 | Goldman et al. | 435/368 |
| 6,251,669 B1 | * 6/2001 | Luskin | 435/375 |

FOREIGN PATENT DOCUMENTS

| | | |
|---|---|---|
| WO | WO 93/01275 | 1/1993 |
| WO | WO 94/02593 | 2/1994 |
| WO | WO 96/38576 | 12/1996 |
| WO | WO 97/07200 | 2/1997 |
| WO | WO 98/32879 | 7/1998 |

OTHER PUBLICATIONS

Friedmann, T. Overcoming the obstacles to gene therapy. Sci. Am. Jun. 1997, pp. 96–101.*
Orkin and Motulsky. Report and recommendations of the panel to assess the NIH investment in research on gene therapy, 1995.*
Verma et al. Gene therapy—promises, problems and prospects. Nature 389: 239–242, 1997.*
Wang et al. Isolation of neuronal precursors by sorting embryonic forebrain transfected with GFP regulated by the Talpha 1 tubulin promoter. Nature Biotechnology 16: 196–201, 1998.*
Weiss et al. there is a neural stem cell in the mammalian forebrain? Trends Neurosci. 19(9): 387–393, 1997.*
Ahmed et al., "BDNF Enhances the Differentation but not the Survival of CNS Stem Cell–Derived Neuroal Precursors," J. Neurosci., 15(8):5765–5778 (1995).

(List continued on next page.)

Primary Examiner—Anne-Marie Falk
(74) Attorney, Agent, or Firm—Nixon Peabody LLP

(57) ABSTRACT

The present invention provides neuronal progenitor cells which have been identified in histological sections of the adult human brain. The present invention also provides methods to localize, characterize, harvest, and propagate neuronal progenitor cells derived from human brain tissue. Additional methods are provided for introducing and expressing genes in the brain.

25 Claims, 6 Drawing Sheets

OTHER PUBLICATIONS

Anderson et al., "A Bipotential Neuroendocrine Precursor whose Choice of Cell Fate is Determined by NGF and Glucocorticoids," *Cell*, 47:1079–1090 (1986).

Barres et al., "A Crucial Role for Neurotrophin–3 in Oligodendrocyte Development," *Nature*, 367:371–375 (1994).

Dahlstrand et al., "Characterizaton of the Human Nestin Gene Reveals a Close Evolutionary Relationship to Neurofilaments," *J. Cell Sci*, 103:589–597 (1992).

DeHamer et al., "Genesis of Olfactory Receptor Neurons in Vitro: Regulation of Progenitor Cell Divisions by Fibroblast Growth Factors," *Neuron*, 13:1083–1097 (1994).

Deloulme et al., "Establishment of Pure Neuronal Cultures from Fetal Rat Spinal Cord and Proliferation of the Neuronal Precursor Cells in the Presence of Fibroblast Growth Factor," *J. Neurosci. Res*, 29:499–509 (1991).

DiCicco–Bloom et al., "Insulin Growth Factors Regulate the Mitotic Cycle in Cultured Rat Sympathetic Neuroblasts," *Proc. Natl. Acad. Sci. U.S.A.*, 85:4066–4070 (1988).

DiCicco–Bloom et al., "NT–3 Stimulates Sympathetic Neuroblast Proliferation by Promoting Precursor Survival," *Neuron*, 11:1101–1111 (1993).

Drago et al., Fibroblast Growth Factor–Mediated Proliferation of Central Nervous System Precursors Depends on Endogenous Production of Insulin–Like Growth Factor I, *Proc. Natl. Acad. Sci. U.S.A.*, 88:2199–2203 (1991).

Gensburger et al., "Brain Basic Fibroblast Growth Factor Stimulates the Proliferation of Rat Neuronal Precursor Cells In Vitro," *FEBS Lett*, 217:1–5 (1987).

Goldman, "Adult Neurogenesis: From Canaries to the Clinic," *J. Neurobiol.* 36:267–86 (1998).

Goldman and Luskin, "Strategies Utilized by Migrating Neurons of the Postnatal Vertebrate Forebrain," *Trends in Neurosci.* 21(3):107–114 (1998).

Gritti et al., "Multipotential Stem Cells from the Adult Mouse Brain Proliferate and Self–Renew in Response to Basic Fibroblast Growth Factor," *J. Neurosci.*, 16:1091–1100 (1996).

Kilpatrick et al., "Cloned Multipotential Precursors from the Mouse Cerebrum Require FGF–2, Whereas Glial Restricted Precursors are Stimulated with Either FGF–2 or EGF," *J. Neurosci.*, 15:3653–3661 (1995).

Kitchens et al., "FGF and EGF are Mitogens for Immortalized Neural Progenitors," *J. Neurobiol.*, 25:797–807 (1994).

Lendahl et al., "CNS Stem Cells Express a New Class of Intermediate Filament Protein," *Cell*, 60:585–595 (1990a).

Lillien et al., "Type–2 Astrocyte Development in Rat Brain Cultures is Intiated by a CNTF–Like Protein Produced by Type–1 Astrocytes," *Neuron.* 1:485–494 (1988).

Lu et al., "A Paradigm for Distinguishing the Roles of Mitogenesis and Trophism in Neuronal Precursor Proliferation," *Dev. Brain Res.*, 94:31–36 (1996).

McKinnon et al., "Distinct Effects of bFGF and PDGF on Oligodendrocyte Progenitor Cells," *Glia*, 7:245–254 (1993).

Murphy et al., "Fibroblast Growth Factor Stimulates the Proliferation and Differentiation of Neural Precursor Cells in Vitro," *J. Neurosci. Res*, 25:463–475 (1990).

Murphy et al., "Generation of Sensory Neurons is Stimulated by Leukemia Inhibitory Factor," *Proc. Natl. Acad. Sci. U.S.A.*, 88:3498–3501 (1991).

Murphy et al., "FGF2 Regulates Proliferation of Neural Crest Cells, with Subsequent Neuronal Differentiation Regulated by LIF or Related Factors," *Development*, 120:3519–3528 (1994).

Palmer et al., "FGF–2 Responsive Neuronal Progenitors Reside in Proliferative and Quiescent Regions of the Adult Rodent Brain," *Mol. Cell. Neurosci.*, 6:474–486 (1995).

Pincus et al., "Vasoactive Intestinal Peptide Regulates Mitosis, Differentiation and Survival of Cultured Sympathetic Neuroblasts," *Nature*, 343:564–567 (1990).

Pincus et al., "Fibroblast Growth Factor–2/Brain–Derived Neurotrophic Factor–Associated Matruation Of New Neurons Generated From Adult Human Subependymal Cells," *Ann. Neurol.*, 43(5):576–585 (1998).

Qian et al., "FGF2 Concentration Regulates the Generation of Neurons and Glia from Multipotent Cortical Stem Cells," *Neuron*, 18:81–93 (1997).

Raff et al., "A Glial Progenitor Cell that Develops In Vitro into an Astrocyte or an Oligodendrocyte Depending on Culture Medium," *Nature*, 303:390–396 (1983).

Raff et al., "Platelet–Derived Growth Factor from Astrocytes Drives the Clock that Time Oligodendrocyte Development in Culture," *Nature*, 333:562–565 (1988).

Ray et al., "Proliferation, Differentiation, and Long–Term Culture of Primary Hippocampal Neurons," *Proc. Natl. Acad. Sci. U.S.A.*, 90:3602–3606 (1993).

Ray et al., "Spinal Cord Neuroblasts Proliferate in Response to Basic Fibroblast Growth Factor," *J. Neurosci.*, 14:3548–3564 (1994).

Reynolds et al., "A Multipotent EGF–Responsive Striatal Embryonic Progenitor Cell Produces Neurons and Astrocytes," *J. Neurosci.*, 12:4565–4574 (1992a).

Reynolds et al., "Generation of Neurons and Astrocytes from Isolated Cells of the Adult Mammalian Central Nervous System," *Science*, 255:1707–1710 (1992b).

Santa–Olalla et al., "Epidermal Growth Factor (EGF), Transforming Growth Factor–$\alpha$ (TGF–$\alpha$), and Basic Fibroblast Growth Factor (bFGF) Differentially Influence Neural Precursor Cells of Mouse Embryonic Mesencephalon," *J. Neurosci. Res.*, 42:172–183 (1995).

Shah et al., "Glial Growth Factor Restricts Mammalian Neural Crest Stem Cells to a Glial Fate," *Cell*, 77:349–360 (1994).

Sieber–Blum, "Role of the Neurotrophic Factors BDNF and NGF in the Commitment of Pluripotent Neural Crest Cells," *Neuron.* 6:949–955 (1991).

Temple et al., "Differentiation of a Biopotential Glial Progenitor Cell in a Single Cell Microculture," *Nature*, 313:223–225 (1985).

Vescovi et al., "bFGF Regulates the Proliferative Fate of Unipotent (Neuronal) and Bipotent (Neuronal/Astroglial) EGF–Generated CNS Progenitor Cells," *Neuron*, 11:951–966 (1993).

Weiss et al., "Is There a Neutral Stem Cell in the Mammalian Forebrain!," *Trends Neurosci.*, 19:387–393 (1996a).

Weiss et al., "Multipotent CNS Stem Cells are Present in the Adult Mammalian Spinal Cord and Ventricular Neuroaxis," *J. Neurosci.*, 16:7599–7609 (1996b).

Wolswijk et al., "Cooperation Between PDGF and FGF Converts Slowly Dividing O–2A$^{Adult}$ Progenitor Cells to Rapidly Dividing Cells with Characteristics of O–2$^{Perinatal}$ Progenitor Cells," *J. Cell. Biol.*, 118:889–900 (1992).

Pincus et al., "In vitro Neurogenesis by Adult Human Epileptic Temporal Neocortex," *Clinical Neurosurgery* 44:17–25 (1997).

Goldman et al., "Neural Precursors and Neuronal Production in the Adult Mammalian Forebrain," *Ann. N.Y. Acad. Sci.* 835:30–55 (1997).

Pincus et al., "FGF2/BNDF–associated Maturation of New Neurons Generated from Adult Human Subependymal Cells," *Annals Neurol.* 43:576–585 (1998).

Barami et al., "Hu Protein as an Early Marker of Neuronal Phenotypic Differentiation by Subependymal Zone Cells of the Adult Songbird Forebrain," *J. Neurobiol.*, 28:82–101 (1995).

Grinspan et al., "Platelet–Derived Growth Factor is a Survival Factor for PSA–NCAM+ Oligodendrocyte Pre–Progenitor Cells," *J. Neurosci. Res.* 41:540–551 (1995).

Kahn et al., "Thérapie Génique des Maladies Neurologiques," *C.R. Soc. Biol.*, 190:9–11 (1996).

Wang, "Isolation of Neuronal Precursors by Sorting Embryonic Forebrain Transfected with GFP Regulated by the T$\alpha$1 Tubulin Promoter," *Nature Biotechnol.*, 16:196–201 (1998).

Pincus et al., "Neural Stem Cells: A Strategy for Gene Therapy and Brain Repair," *Neurosurgery*, 42(4):1–11 (1998).

* cited by examiner

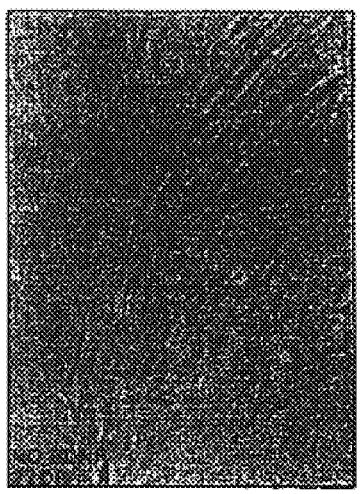
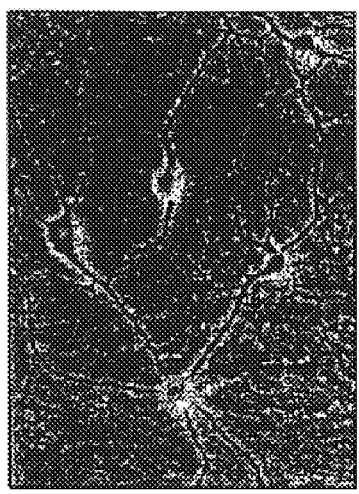
*FIG. 1A*  *FIG. 1B*  *FIG. 1C*

DISCOVERY, LOCALIZATION, HARVEST, AND PROPAGATION OF AN FGF2 AND BDNF-RESPONSIVE POPULATION OF NEURAL AND NEURONAL PROGENITOR CELLS IN THE ADULT HUMAN FOREBRAIN

The present application claims the benefit of U.S. Provisional Patent Application Ser. No. 60/079,226 filed Mar. 25, 1998.

The subject matter of this application was made with support from the United States Government under Grant Nos. NINDS RO1NS33106 and NINDS RO1NS29813 from the National Institutes of Health. The United States Government may retain certain rights.

FIELD OF THE INVENTION

The present invention relates to neuronal progenitor cells which have been identified in both tissue cultures and histological sections of the adult human brain. The present invention provides methods for the localization, characterization, harvest, and propagation of neuronal progenitor cells derived from adult humans.

BACKGROUND OF THE INVENTION

The damaged adult mammalian brain is incapable of significant structural self-repair. Terminally differentiated neurons are incapable of mitosis, and compensatory neuronal production has not been observed in any mammalian models of structural brain damage (Korr, 1980; Sturrock, 1982). Although varying degrees of recovery from injury are possible, this is largely because of synaptic and functional plasticity rather than the frank regeneration of neural tissues. The lack of structural plasticity of the adult brain is partly because of its inability to generate new neurons, a limitation that has severely hindered the development of therapies for neurological injury or degeneration. Indeed, the inability to replace or regenerate damaged or dead cells continues to plague neuroscientists, neurologists, and neurosurgeons who are interested in treating the injured brain. During the last several years, however, a considerable body of evidence has evolved that suggests a marked degree of cellular plasticity in the adult as well as in the developing CNS. In particular, recent work on neural progenitor cells, derived from both embryos and adults, has suggested strategies for directed neuronal regeneration and structural brain repair. These include the use of neural stem cells which are the multipotential progenitors of neurons and glia that are capable of self-renewal (Davis, 1994; Gritti, 1996; Kilpatrick, 1993; Morshead, 1994; Stemple, 1992; Goldman, 1996; Weiss, 1996a).

In the adult human brain, both neuronal and oligodendroglial precursors have been identified as well, and methods for their harvest and enrichment have been established. Neural precursors have several characteristics that make them ideal vectors for brain repair. They may be expanded in tissue culture, providing a renewable supply of material for transplantation. Moreover, progenitors are ideal for genetic manipulation and may be engineered to express exogenous genes for neurotransmitters, neurotrophic factors, and metabolic enzymes (reviewed in Goldman 1998; Pincus 1998; and Goldman & Luskin 1998).

In embryonic neurogenesis, the proliferation of neuronal precursors takes place at the surface of the central canal lining the neural tube (Jacobson, 1991). The central canal ultimately forms the ventricular system of the adult. This neurogenic layer is referred to as the ventricular/subventricular zone in development, and the ependymal/subependymal zone (SZ) in adults (Boulder Committee, (1970). In development, mitogenesis in the ventricular/subventricular zone is followed by the migration of newly generated neurons and glia along radial guide fibers into the brain parenchyma, including that of the cortical plate (LaVail, 1971; Rakic, 1971; Rakic, 1974; Sidman, 1973).

A variety of signals, including both humoral and contact-mediated factors, have been described which influence the proliferation, differentiation, and survival of stem cells and their progeny. Work on model systems derived from the peripheral nervous system has suggested that the neurotrophins (Anderson, 1986; DiCicco-Bloom, 1993; Murphy, 1991; Sieber-Blum, 1991), neurotransmitters (Pincus, 1990), and traditional growth factors (DiCicco-Bloom, 1988; Murphy, 1994; Shah, 1994) may all influence the development of precursors in vitro. In the CNS, soluble growth factors, particularly basic fibroblast growth factor (FGF-2) regulate neuronal precursor proliferation (DeHamer, 1994; Deloulme, 1991; Drago, 1991; Gensburger, 1987; Gritti, 1996; Kilpatrick, 1995; Kitchens, 1994; Murphy, 1990; Palmer, 1995; Qian, 1997; Ray, 1994; Ray, 1993; Vescovi, 1993). In mixed cell cultures derived from rat embryonic cerebrum, the addition of FGF-2 stimulated the proliferation of neuronal precursors (Gensburger, 1987). Similarly, FGF-2 stimulated the proliferation of a multipotential neural progenitor in fetal mice, which gave rise to neurons and astrocytes (Kilpatrick, 1995). Embryonic rat hippocampal, spinal cord, and olfactory neuron progenitors all have been shown to proliferate in the presence of FGF-2 (DeHamer, 1994; Deloulme, 1991; Ray, 1994; Ray, 1993). Not surprisingly, FGF-2 may also regulate precursor division in concert with other factors; this has been demonstrated in the coordinate regulation of neuronal precursor division by insulin-like growth factor I and FGF-2 (Drago, 1991), as well as oligodendrocyte precursor division by FGF-2 and platelet-derived growth factor (McKinnon, 1993; Wolswijk, 1992).

Where FGF2 had been shown to promote the division of neuronal precursor cells and, hence, the specific generation of neurons, epidermal growth factor (EGF) has also been shown to influence the proliferation of uncommitted neural precursors (Kitchens, 1994; Lu, 1996; Ray, 1994; Reynolds, 1992b; Reynolds, 1992a; Santa-Olalla, 1995; Weiss, 1996b). In dissociated cultures of embryonic mouse striata grown in suspension without culture substrata, EGF induced the proliferation of progenitor cells and the formation of floating "neurospheres" of cells, which expressed nestin (Reynolds, 1992a). Nestin is an intermediate filament protein expressed not only by CNS stem cells (Dahlstrand, 1992; Lendahl, 1990a), but also by young neurons reactive astrocytes, and radial glia. When these neurospheres were dissociated and plated onto poly-L-ornithine-coated plates, γ-aminobutyric acid- and substance P-expressing neurons and glial fibrillary acidic protein-expressing astrocytes were generated (Ahmed, 1995). Similar effects were reported in adult striatal cultures (Reynolds, 1992b). In this culture preparation, the actions of EGF were mimicked by its membrane-bound homolog, transforming growth factor α, but not by nerve growth factor, FGF-2, platelet-derived growth factor, or transforming growth factor β. A similar action of EGF on precursor cells derived from embryonic and adult rat spinal cord has also been reported (Ray, 1994; Weiss, 1996).

Although it is now possible to isolate and cultivate populations of neural precursors in vitro, the ability to direct specific neuronal phenotypes has remained elusive. In the EGF-generated sphere model, multipotent progenitors differentiated into neurons, which expressed γ-aminobutyric acid and substance P, as well as astrocytes and oligodendrocytes (Reynolds, 1992b; Reynolds, 1992a; Vescovi, 1993; Weiss, 1996b). Other neuronal phenotypes were rare, and their directed differentiation into defined transmitter phenotypes has not yet been demonstrated. In this regard, Raff et al. (Raff, 1988; Raff, 1983) suggested that growth factors control the development of a bipotential glial progenitor. Sequential exposure to specific combinations of platelet-derived growth factor, ciliary neurotrophic factor, and neurotrophin 3 can direct clonal expansion of the oligodendrocyte/Type 2 astrocyte (O2A) progenitor cell in vitro, and drive an intrinsic clock that times oligodendrocyte development (Barres, 1994; Lillien, 1988; Raff, 1988; Temple, 1985). Nonetheless, a similarly directed differentiation of multipotent stem cells along specific neuronal lines has not yet been clearly demonstrated.

The persistence of neuronal precursors in the adult mammalian brain may permit the design of novel and effective strategies for central nervous system repair. However, although methods for the characterization and propagation of progenitors derived from adult rodents have been described, no such methods have allowed the high-yield harvest of purified native progenitors. Furthermore, no methods have been reported for obtaining or propagating such progenitor cells from adult human brain tissue.

SUMMARY OF THE INVENTION

The present invention provides human neural or neuronal progenitor cells isolated and enriched from non-embryonal brain tissue of a human.

Another aspect of the present invention is a method of propagating neurons from progenitor cells derived from brain tissue by serially applying FGF2 and BDNF to the cells.

The present invention also provides a method of treating neurological damage by transplanting or implanting neuronal progenitor cells into the brain of a human patient. Human neuronal progenitor cells isolated from an adult human using the methods of the present invention are transplanted or implanted into the brain of a patient.

Yet another aspect of the invention is a method of enhancing the survival and function of neural or neuronal precursor cells or the cells descended from the neural or neuronal precursor cells by transducing the neural or neuronal precursor cells with a gene encoding an autocrine neurotrophin or an adhesion molecule.

A further embodiment of the invention is a method of treating a patient with a neurological disease resulting from the loss of expression or mutation of a gene required for neuronal function. A gene which encodes a functional protein which complements the loss of expression or mutation of the gene required for neuronal function is transfected into postnatal or adult human neuronal progenitor cells. The neuronal progenitor cells are then introduced into the brain of the patient.

The present invention also provides a method of detecting neural or neuronal progenitor cells. An antibody, which is directed against an RNA binding protein that is selectively and specifically expressed by neural or neuronal progenitor cells when compared to other cell types, is contacted with cells and those cells which are bound by the antibody are detected.

The present invention also relates to a method of separating human, non-embryonal neural or neuronal progenitor cells from a mixed population of cells from human brain tissue. In accordance with this method, a promoter which functions only in the human postnatal neural and neuronal progenitor cells is selected. A nucleic acid molecule encoding a fluorescent protein, under control of said promoter, is then introduced into the mixed population of cells. The non-embryonal neural or neuronal progenitor cells thereof are allowed to express the fluorescent protein. The fluorescent cells are separated from the mixed population of cells, where the separated cells are the neural or neuronal progenitor cells.

Yet another embodiment of the invention is a method of expressing a gene in the brain of a patient. Adult human neuronal progenitor cells are isolated. The cells are transformed with a gene and are then transplanted into the brain of a patient. The gene is then expressed in the brain of the patient.

Prior to this invention, a method for progenitor cells were only available from embryos. However, this source is problematic due to legal and ethical concerns resulting from the harvesting of embryonic tissue. Furthermore, the embryonic tissue may not be immunologically compatible with the patient's tissue. The present invention provides a method for isolating and propagating progenitor cells isolated from the brain tissue of an adult human. The isolated progenitors can then be propagated in vitro or in vivo to treat nervous system damage. This method provides a non-embryonic source of progenitor cells, that may be derived from the patient's own tissue.

BRIEF DESCRIPTION OF THE DRAWINGS

FIGS. 1A–1C show that cultures of the adult rat SZ typically display a burst of neuronal outgrowth during the first 11 days in vitro (DIV) but suffer virtually complete neuronal loss during the 2 weeks thereafter. However, in the presence of BDNF (20 ng/ml), new adult neurons survived substantially longer than did their counterparts grown in unsupplemented media. FIG. 1A shows adult rat SZ neurons grown in control medium after 22 days. FIGS. 1B and 1C show sister cultures grown in BDNF after 36 and 57 days in vitro, respectively.

FIGS. 2A–B are pre- and post-operative coronal MRI images of a 37 year-old female with refractory epilepsy and radiographic mesial temporal sclerosis. FIG. 2A shows atrophic sclerosis of the right hippocampus and dentate gyrus (arrow). FIG. 2B is of the same patient, 2 weeks after surgical resection. FIG. 2C shows a schematic coronal view of temporal lobe, showing the subventricular region typically sampled for culture. Cortical specimens were typically obtained from the adjacent inferior temporal gyrus (modified with permission from Kirschenbaum et al., 1994 (Kirschenbaum, 1994, which is hereby incorporated by reference)).

FIG. 3A is a phase micrograph of two adjacent cells, one neuron-like and the other astrocytic. Scale bar=25 μm. FIG. 3B shows their baseline levels of $Ca^{2+}_i$, as viewed by confocal microscopy with laser scanning at 488 nm. FIG. 3C depicts the same two cells within seconds after exposure to 60 mmol/

K+. The neuron-like cell increased its $Ca^{2+}_i$ rapidly and reversibly, in contrast to the cocultured astrocytes. FIG. 3D shows that with the addition of tetrodotoxin (TTX) (1 µmol/L; Sigma Chemical Co., St. Louis, Mo.), K+-stimulation yielded a more than sixfold rise in neuronal cytosolic $Ca^{2+}_i$, whereas astrocytic $Ca^{2+}_i$ increased less than twofold. The depolarization-induced $Ca^{2+}$ increment of this cell suggested its neuronal phenotype, as did the TTX accentuation of its $Ca^{2+}_i$ response. The increased density of TTX-sensitive Na+ channels in neurons, relative to glia, would have been expected to yield a neuron-selective enhancement of the K+-stimulated $Ca^{2+}_i$ response by TTX. FIG. 3E, at withdrawal of K+ from the medium, each cell returned to its resting $Ca^{2+}_i$ level. FIG. 3F, after addition of the calcium inophore lasalocid (50 mmol/L, Sigma), added as a positive control to maximize $Ca^{2+}$ entry in both cells. These results suggested the activity of voltage-gated calcium channels in the adult-derived neurons. FIGS. 3G and 3H show cultures which were stained for neuron-specific antigens and were subjected to $^3$H-thymidine autoradiography. FIG. 3G depicts a MAP-5+ cell observed in dissociate culture after 15 days in vitro. FIG. 3H shows a cell which has incorporated $^3$H-thymidine in vitro, suggesting its origin from precursor mitosis (Kirschenbaum, 1994, which is hereby incorporated by reference).

FIGS. 4A–B show scattered islands of subependymal cells expressed the neural progenitor cell marker musashi. These sections were immunoperoxidase stained for musashi using anti-mouse musashi IgG. FIGS. 4C–D show loose aggregates of adult SZ cells also expressed Hu proteins, a triad of early, neuron-specific RNA-binding proteins recognized by MAb 16A11 (Baram, et al., 1995; Szabo, et al. 1991, which are hereby incorporated by reference). Immunostaining revealed frequent pockets of Hu+ scattered about the ventricular epithelium (Scale=50 µm.).

FIG. 5A shows cell outgrowth from adult human SZ, 9 wks in vitro. The explant was exposed to FGF2 for a week, in the presence of $^3$H-thymidine, then to BDNF for 2 months, then fixed and stained for the neuronal marker MAP-2. FIG. 5B shows that two of these MAP-2+ neurons incorporated $^3$H-thymidine during their first week in vitro (aggregations of silver grains denoted by arrows), indicating mitotic neurogenesis during the period of FGF2 exposure. FIG. 5C is a high power visualization of the cell asterisked in FIGS. 5A–B, stained for MAP-2. FIG. 5D shows the cells after $^3$H-thymidine autoradiography. FIG. 5E is another outgrowth from an adult temporal SZ explant, 7 weeks in culture. This sample was also raised in FGF2 followed by BDNF, then subjected to confocal imaging of the fluorescence signal emitted by the calcium indicator dye fluo-3; this was done to assess neuronal responses to depolarizing stimuli. FIG. 5F depicts the baseline fluo-3 fluorescence signal from the neurons indicated in phase in 5E (arrows). FIG. 5G was taken immediately after depolarization by 60 mM KCl. A similar response to 10 µM glutamate was observed. In each of these photos, the Scale=25 µm.

FIG. 6A shows a field of neurons found in a temporal neocortical explant culture after 9 wks in vitro, revealing a congregation of neurons lying upon a field of ependymal cells and glia. This culture was derived from a 28 year-old man, and was treated sequentially with FGF-2 (1 wk) and BDNF (8 wks). The asterisk in FIG. 6A corresponds to the same position as that in FIGS. 6B–E. FIG. 6B is a higher magnification within FIG. 6A (note: FIGS. 6B–E are rotated 90° counter-clockwise with respect to FIG. 6A). FIG. 6C demonstrates that immunostaining for MAP-2 indicates the neuronal identity of these cells. FIG. 6D provides the baseline calcium signal of these neurons which was determined by confocal imaging their emission to argon laser excitation at 488 nm, after loading the cells with fluo-3. FIG. 6E shows the marked increase in fluo-3 fluorescence typical of the neuronal calcium response to K+-depolarization. FIGS. 6F–G shows that of 11 MAP-2+ cells in FIG. 6B, four were found to have incorporated $^3$H-thymidine+; two of these are shown after $^3$H-thymidine autoradiography in FIG. 6F (arrows, in phase), and after staining for MAP-2 in FIG. 6G. The remaining seven neurons in FIG. 6B may have been cells that committed to neuronal differentiation without intervening cell division.

DETAILED DESCRIPTION OF THE INVENTION

The present invention provides neuronal progenitor cells isolated from the non-embryonal tissue of the human brain. This novel population of cells can be isolated from the ependymal layer or the subependymal layer of the adult human brain. A preferred embodiment of the present invention is where the cells are isolated from the temporal subependyma.

Figure 2A:
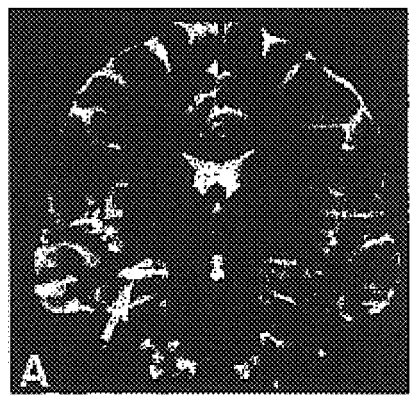
FIGS. 2A–2C show a region sampled for culture and immunohistology.
Figure 2B:
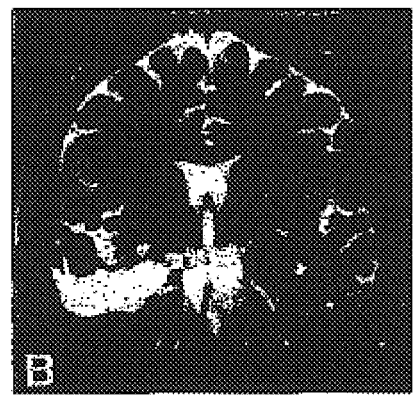
Figure 2C:
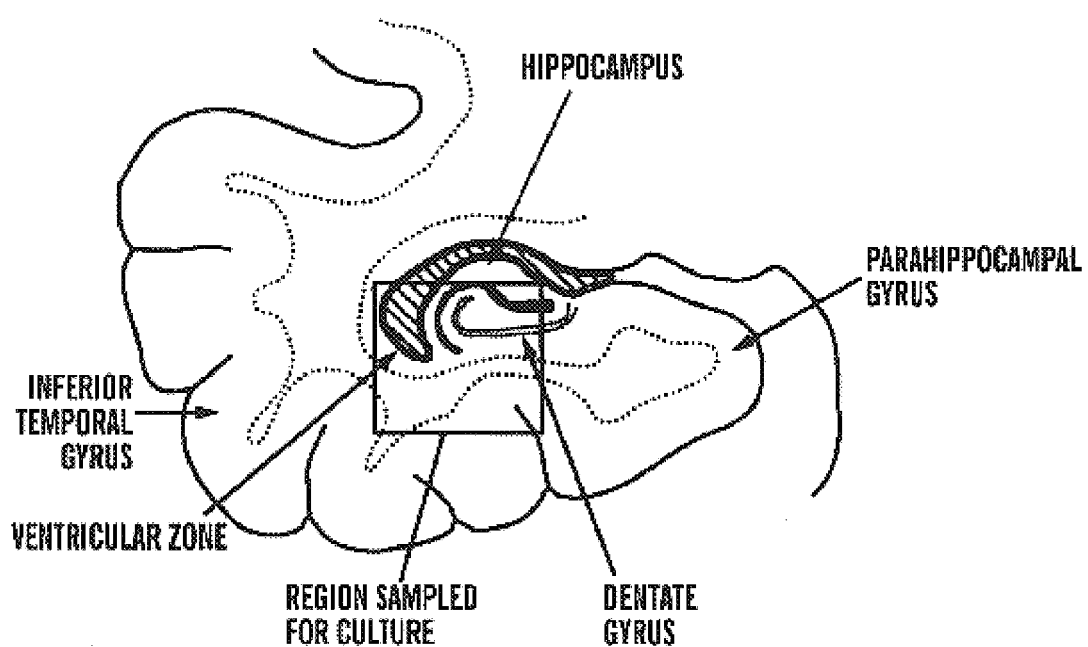
Figure 3A:
FIGS. 3A–3H shows that human temporal SZ-derived neurons are physiologically active and are the product of neurogenesis in vitro. A–F, cultures were challenged with high $K^+$ to seek evidence of neuron-like depolarization-induced increments in cytosolic calcium ($Ca^{2+}_i$). In this plate, a temporal SZ culture was tested after 28 days in vitro, after loading with the $Ca^{2+}$-sensitive dye fluo-3.
Figure 3B:
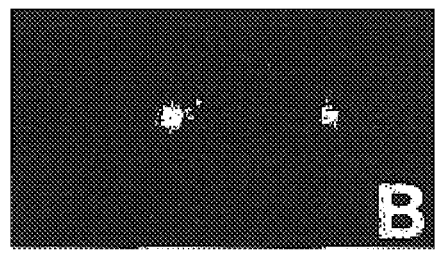
Figure 3C:
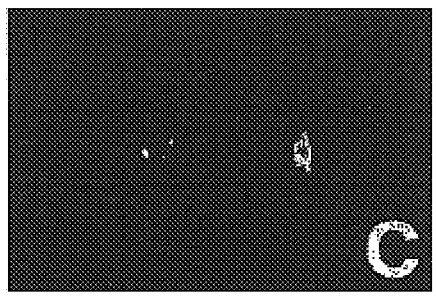
Figure 3D:
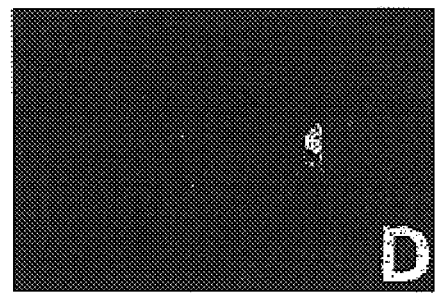
Figure 3E:
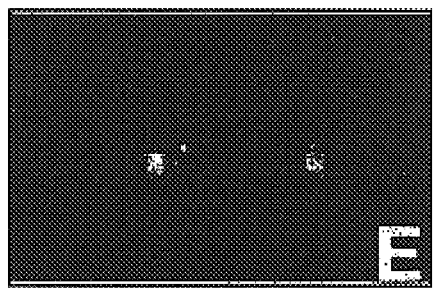
Figure 3F:
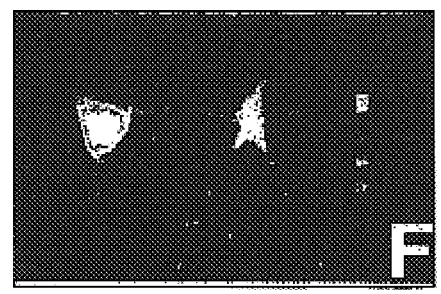
Figure 3G:
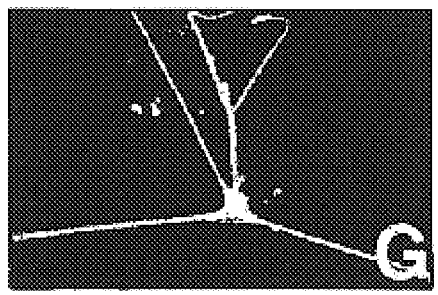
Figure 3H:
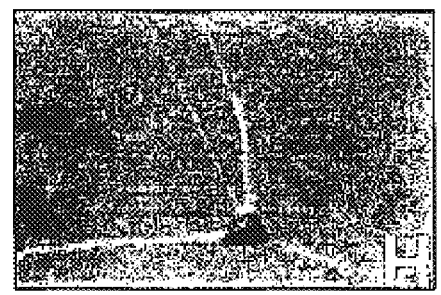
Figure 4A:
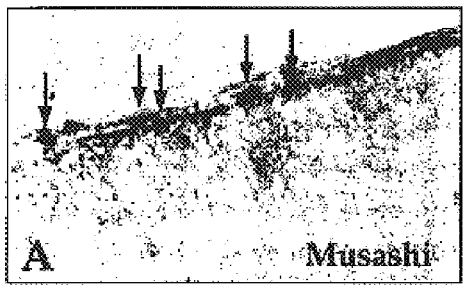
FIGS. 4A–4D demonstrate that the adult human subependyma harbors scattered islands of apparent progenitor cells. The ependyma/subependyma lining the temporal horn of the lateral ventricle, deep to the inferior temporal gyrus, in a 27 year-old man with mesial temporal sclerosis is shown. This region had distinct squamous ependymal and cuboidal subependymal layers, each 1–2 cells deep.
Figure 4B:
Figure 4C:
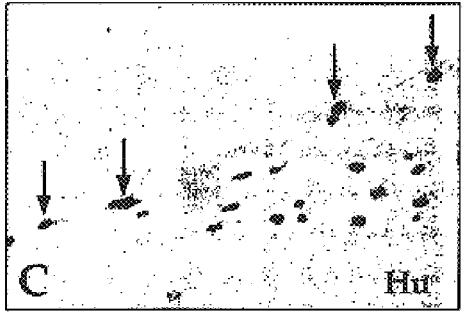
Figure 4D:
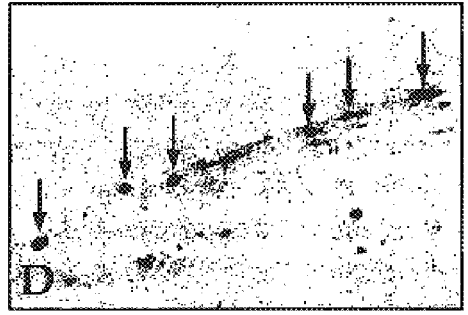
Figure 5A:
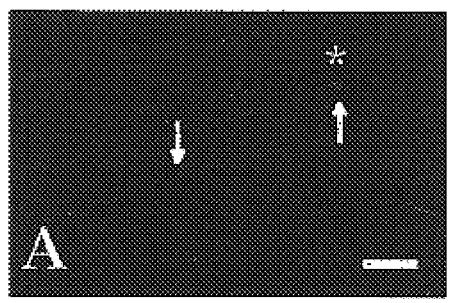
FIGS. 5A–5G demonstrate that serial treatment with fibroblast growth factor-2 ("FGF2") and brain-derived neurotrophic factor ("BDNF") allows for the expansion and survival of neurons arising from human subependymal zone ("SZ").
Figure 5B:
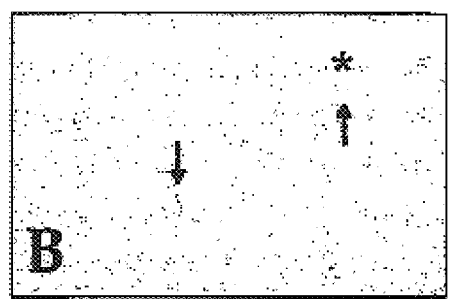
Figure 5C:
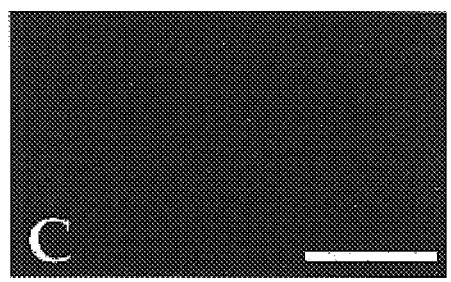
Figure 5D:
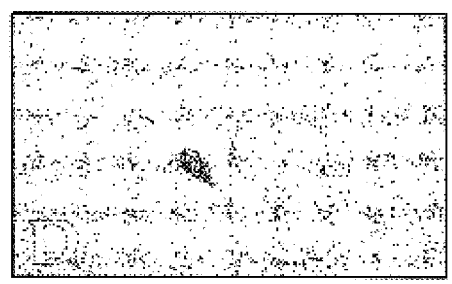
Figure 5E:
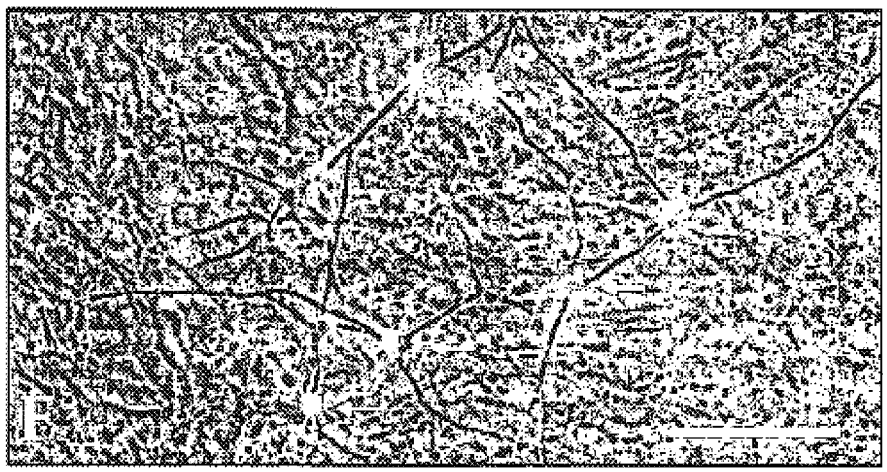
Figure 5F:
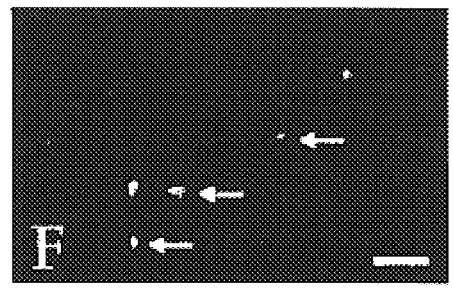
Figure 5G:
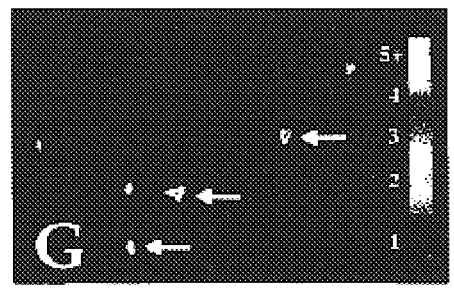
Figure 6A:
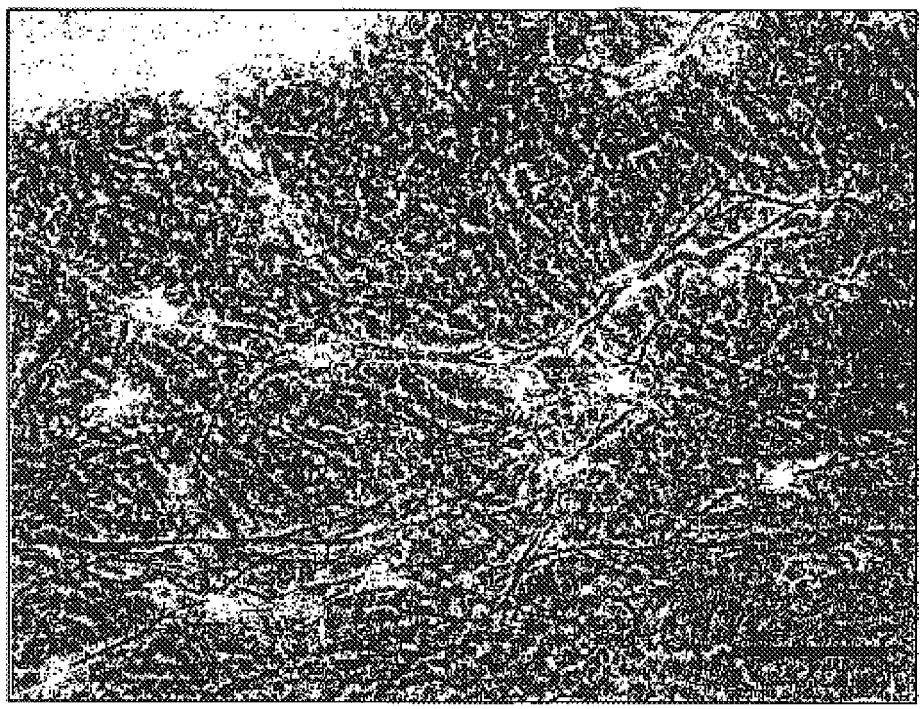
FIGS. 6A–6G show that rare neocortical explants also exhibited neuronal production and outgrowth. In cultures derived from 2 patients, neuronal outgrowth was noted from explants derived from both the SZ and cortex. This suggested that temporal cortex might harbor residual neuronal precursors, analogous to those of the SZ.
Figure 6B:
Figure 6C:
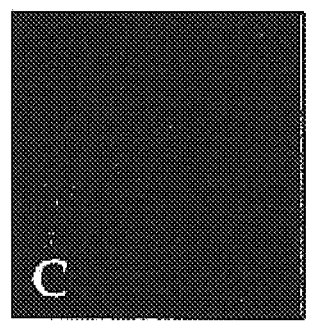
Figure 6F:
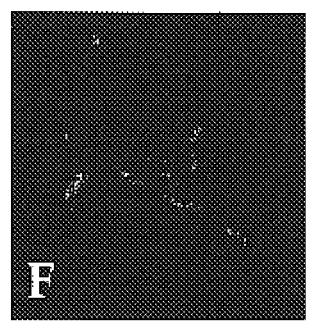
Figure 6D:
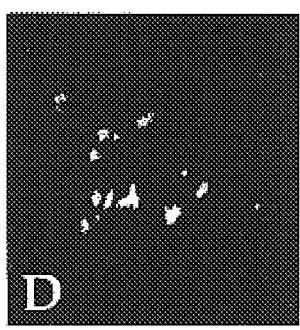
Figure 6E:
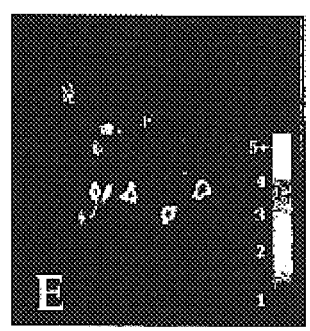
Figure 6G:
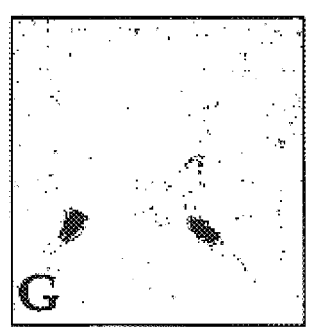

To identify neuronal precursor cells which persist in the adult human brain, methods were developed to culture SZ explants derived from adult human temporal lobes, removed for the treatment of intractable epilepsy (Kirschenbaum, 1994 and Pincus 1998, which are hereby incorporated by reference). Specimens were divided into cortical, subcortical, and periventricular zone-derived groups and were explanted into tissue cultures using techniques previously established for the adult canary and rat brain (Goldman, 1990; Goldman, 1992a; Kirschenbaun 1995, which are hereby incorporated by reference). Both explants and monolayer cultures of the SZ yielded neurons, whose identity was confirmed by immunolocalization of a panel of neuron-selective antigens. In rare cases, new neurons were also generated from neocortical tissue. Furthermore, temporal SZ dissociates exposed to $^3$H-thymidine in culture yielded $^3$H-thymidine-labeled, microtubule-associated protecin 2-expressing cells, indicative of neurons newly generated in vitro (FIG. 2). Of note, the neurons generated by these precursors assume neuronal function as well as antigenicity. Confocal calcium imaging of neurons migrating from adult human SZ explants showed that they responded to both potassium depolarization and glutamate with sharp increases in cytosolic calcium, indicating their development of mature neuronal response characteristics (FIG. 3).

A preferred type of human progenitor cells express an RNA-binding protein which characterizes early neural or neuronal phenotype. More particularly, to identify neural progenitor cells and their daughters in vivo, brain samples were immunostained for RNA-binding proteins that characterize early neural or neuronal phenotypes, the musashi and Hu proteins, respectively. In a preferred embodiment of the invention the RNA-binding protein that characterizes the early uncommitted neural phenotype is musashi. Musashi, a 39 kD RNA-binding protein initially described in Drosophila and Xenopus, is expressed in development by mitotic neural progenitors, including CNS stem cells. In the adult rat brain, musashi expression is limited to progenitor cells of the lateral ventricular and olfactory subependyma. It is not expressed by mature neurons or oligodendrocytes, but is expressed at a low level by parenchymal astrocytes. In an alternative embodiment of the invention, the RNA-binding protein that characterizes the early neuronal phenotype is a Hu protein. In contrast to Musashi, Hu comprises a family of 35–42 kD proteins, at least three of which, HuD, HuC, and HelN1, are expressed selectively by neurons and their committed post-mitotic progenitors. HuD, HuC, and HelN1 are preferred embodiments of the Hu protein. In the CNS, Hu appears very early in neuronal ontogeny, but is not expressed by cycling progenitors; it is thus an effective marker for neuronal daughter cells still within the SZ (Baram, et al., 1995, which is hereby incorporated by reference).

In preferred embodiments, cells are isolated from patients with epilepsy, requiring brain tissue resection for treatment of trauma, cerebral edema, or aneurysmal repair.

The present invention also relates to a method of separating human, non-embryonal neural or neuronal progenitor cells from a mixed population of cells from human brain tissue. In accordance with this method, a promoter which functions only in the human non-embryonal neural and neuronal progenitor cells is selected. A nucleic acid molecule encoding a fluorescent protein, under control of said promoter, is then introduced into the mixed population of cells. The non-embryonal neural or neuronal progenitor cells thereof are allowed to express the fluorescent protein. The fluorescent cells are separated from the mixed population of cells, where the separated cells are the non-embryonal neural or neuronal progenitor cells. This procedure is more fully described in U.S. patent application Ser. No. 08/787,788, now U.S. Pat. No. 6,245,564 which is hereby incorporated by reference.

Illustrations of possible cell and promoter combinations which can be used in accordance with the present invention include: a neuronal progenitor and an NCAM promoter (Holst et al. 1994, which is hereby incorporated by reference); a neuronal progenitor and an α1-tubulin promoter (Gloster et al. 1994, which is hereby incorporated by reference); neuronal or neural progenitors and the musashi protein promoter (Nakamura 1994; Richter 1990; Sakakibara 1996; and Sakakibara 1997, which are hereby incorporated by reference); and neuronal or neural progenitors and a Hu protein promoter (Szabo 1991, which is hereby incorporated by reference).

This approach was first established as a means of separating neuronal progenitors from a mixed cell population, using the early neuronal Tα1 tubulin promoter (Wang, 1998, which is hereby incorporated by reference). However, this technique is equally amenable to use with other promoters, such as the tyrosine hydroxylase promoter activated in dopaminergic neurons. As such, this technique may facilitate the selection of transmitter-defined neurons, such as dopaminergic cells, for implantation.

The present invention provides a method of propagating neurons from human progenitor cells isolated from the brain, by serially applying fibroblast growth factor-2 ("FGF-2") and brain-derived neurotrophic factor ("BDNF") to the cells. FGF-2 and BDNF support progenitor division and neuronal maturation and viability, respectively. The effect of both are enhanced by simultaneous treatment with insulin-like growth factor-1 (i.e. IGI-1), which is added to tissue cultures together with FGF2 and BDNF.

In one embodiment, the cells are propagated in culture. In a preferred embodiment, the progenitor cells being propagated and differentiated are derived from fetal brain tissue. Alternatively, the brain cells being propagated and differentiated are derived from juvenile or adult brain tissue.

The method of the present invention may also be used to stimulate neuronal precursors and induce the formation of neurons in situ, for example with FGF2 and/or BDNF intraventricular injection (Kirschenbaum 1995; Pincus et al. 1998; and Zigova et al. 1998, which are hereby incorporated by reference). For in situ treatment, the brain tissue may be that containing from endogenous subependymal or cortical progenitors. Various benefits of in situ treatment are discussed more fully below.

The persistence of such neuronal precursors in the adult brain as well as the isolation of stem cells lines may be exploited clinically in several ways. The most obvious strategy for brain repair is transplantation. The present invention provides a method for treating neurological damage by transplanting or implanting neuronal progenitor cells into a human brain.

In a preferred embodiment of the invention, the neuronal progenitor cells are transplanted or implanted into the subendyma of the neonatal or juvenile human ventricular wall, for the treatment of perinatal brain injury, germinal matrix hemorrhage, or cerebral palsy.

In another preferred embodiment of the invention, the method of transplanting or implanting neuronal progenitor cells into the brain is used to treat Parkinson's Disease. Transplantation has been used in the treatment of 1-methyl-4-phenyl-1,2,3,6-tetrahydropyridine-induced and idiopathic Parkinson's Disease by implantation of fetal mesencephalon (Freed, 1993; Spencer, 1992; Widner, 1992, which are hereby incorporated by reference). However, the difficulties with the use of fetal material are many fold; tissue availability remains a problem, and political and ethical issues continue to hamper progress in this field. Considering these problems, the future of cellular replacement in the nervous system requires additional sources of transplantable material. The use of cultured neuronal cell lines would potentially obviate these difficulties (Snyder, 1997, which is hereby incorporated by reference). Whereas the best source of material for the establishment of new cell lines will likely remain fetal brain, the number of fetuses necessary should be relatively few in comparison to that required for transplantation of primary material. Although the implantation of fetal mesencephalic cells had been limited by the relative scarcity of dopaminergic progenitors in the grafts, the approaches to separating specific transmitter phenotypes may allow the enrichment of desired cell types described above. These techniques are based on fluorescence-activated cell sorting of cells transfected with fluorescent transgenes placed under the control of cell-specific promoters (Wang, 1998, which is hereby incorporated by reference).

In another embodiment of the invention, transplantation or implantation of adult neural progenitors may be used to treat a demyelinating disease. Transplantation or implantation of isolated and/or expanded human progenitors may also be used to treat ischemic brain damage, stroke, or traumatic brain injury.

As an alternate strategy, the presence of precursors in adult brain suggests a potential autologous source for the generation of cultured lines, which may then be reimplanted into the donor (Gage, 1995; Suhonen, 1996, which are hereby incorporated by reference).

Another embodiment is that cultured adult neuronal or neural progenitors may be immortalized by transduction or transfection with immortalizing oncogenes such as v-myc or the large T antigen of SV40 virus (e.g. Flax et al., 1998, which is hereby incorporated by reference, for use with fetal progenitors).

Another approaches may also be used for the possible treatment of demyelinating disease. Oligodendrocyte Type 2 astrocyte progenitors have been injected into demyelinating lesions in adult rat (Franklin, 1996; Gensert, 1997; Groves, 1993, which are hereby incorporated by reference) or canine (Archer, 1997, which is hereby incorporated by reference) spinal cord and are capable of producing extensive remyelination. Further, in addition to neuronal precursor pools, analogous progenitors for oligodendrocytes persist in the mature human brain (Armstrong, 1992; Kirschenbaum, 1994; Scolding, 1995, which are hereby incorporated by reference).

The isolated neuronal progenitor cells may be transformed with a number of therapeutic genes.

In a preferred embodiment, the gene encodes an autocrine neurotrophin. Preferred autocrine neurotrophins include FGF2, BDNF, and IGF1. The invention also provides neuronal precursor cells transformed with a gene encoding an autocrine neurotrophin.

In another preferred embodiment, the gene encodes an adhesion molecule. Preferred adhesion molecules include N-CAM, NgCAM, other members of the immunoglobulin family of adhesion molecules, a member of the integrin-family of proteins, or a member of the connexin family of proteins. The invention provides neuronal precursor cells transformed with a gene encoding an adhesion molecule.

The nucleic acid molecule encoding a gene which is to be expressed can be inserted into a suitable host cell. Various methods for transforming host cells are known in the art. Preferred methods include microinjection, the DEAE-dextran method, electroporation, diffusion, or the use of viral vectors. Preferred viral vectors include retroviruses, adenoviruses, adenoassociated viruses, herpesviruses, and lentiviruses.

The adult human-derived progenitor cells of the present application may also be used as vectors for cell-based gene therapy (Lacorazza and Snyder, which are hereby incorporated by reference). In addition to strategies directed at replacing a particular cell type lost to neurodegenerative disease, progenitor cells may also serve as a vector for gene therapy. The present invention provides a method of expressing a gene in the brain of a patient. Human neuronal progenitor cells are isolated from an adult human and transformed with the gene of interest. The transformed progenitor cells are then transplanted into the brain of the patient.

The present invention also provides a method of enhancing the survival and function of neural or neuronal precursor cells or cells descending from the neural or neuronal precursor cells. This enhancement is carried out by transducing the neural or neuronal precursor cells with a gene encoding an autocrine neurotrophin or an adhesion molecule.

Yet another embodiment of the invention provides a method of detecting neural or neuronal progenitor cells. An antibody directed against a protein, which is preferentially associated with neural or neuronal progenitor cells when compared to other cell types, is contacted with cells. The cells which bind to the antibody are then detected.

Another strategy allows the selective harvest of these cells. Enzymatic dissociation of the adult human ventricular lining and/or brain parenchyma is followed by transfection with plasmid DNA containing a progenitor specific promoter sequence placed 5' to reporter genes (e.g., lacz or GFP). Progenitors, defined by the transcriptional activation of the introduced promoter sequences and consequent expression of the fluorescent reporter gene), can than be identified and viably selected via FACS.

The present invention further provides a method of expressing a gene in the brain of a patient. Isolated adult human neuronal progenitor cells are transformed with the gene. The transformed cells are transformed into the brain of a patient. Once implanted, the gene is expressed in the brain of the patient.

EXAMPLES

Example 1

Materials and Methods
Tissue Samples

Adult human temporal lobe was obtained during anterior temporal lobectomy, performed for the treatment of medically-refractory epilepsy (FIG. 4). The study was limited to patients not known to harbor tumor of any origin, and excluded patients with either radiographically or pathologically-identified dysplasias. The sample included 16 patients, ranging from 6 months to 55 years of age (9 males and 7 females). Approval was obtained from both the New York Hospital-Cornell and Columbia-Presbyterian Institutional Review Boards. Pre-operative MRI was performed on all patients, among whom the most common finding was medial temporal sclerosis (FIG. 4), although several were radiographically normal. Three patients with radiographic cortical dysplasias were excluded from the study. Routine post-operative pathologic examination of the cortex and hippocampus, with hematoxylin and eosin staining of 10 $\mu$m paraffin sections, typically revealed neuronal drop-out and marginal sclerosis, consistent with temporal sclerosis. No occult glioma or other neoplasia was found in these samples.

Culture Preparation

Resections were dissected into neocortical and periventricular samples, the latter including both the ependymal and subependymal layers jointly denoted as subependymal/ependymal zone, SZ). Explant cultures were prepared as described (Kirschenbaum, 1994, which is hereby incorporated by reference). In brief, tissue samples was cut into roughly 0.3 mm$^3$ explants, that were plated on murine laminin in 35 mm petri dishes (Falcon Primaria), and cultured at 37° C. in 5% $CO_2$/95% air.

Media

Cultures were grown in Dulbecco's modified Eagle's medium/Ham's F-12, supplemented with N2 (Bottenstein, 1979, which is hereby incorporated by reference), 15 mM HEPES, 8.5 mg/ml glucose, 6.5 mM L-glutamine, 1.5 mM sodium pyruvate, 30 ng/ml tri-iodothyronine, 1.35 mg/ml bovine serum albumin, 10 mM non-essential amino acids, 40 U/ml penicillin/streptomycin, and 5% fetal bovine serum (Gibco). For the first week in vitro, explants were grown in this base medium, with or without added FGF2 (20 ng/ml); all cultures were exposed to $^3$H-thymidine (0.25 $\mu$Ci/ml) during the first week, but not thereafter. The cultures were then switched to media containing 10% FBS at 8 DIV, half with and half without added BDNF (20 ng/ml; Regeneron).

All plates received half-volume changes with their test media twice weekly.

Immunocytochemistry

In vitro. Cultures were incubated for up to 9 weeks, fixed with 4% paraformaldehyde, and immunostained for the neuron-selective protein MAP-2 (microtubule associated protein-2;) (Bernhardt, 1984, which is hereby incorporated by reference). Two different rabbit anti-MAP-2 antisera were used (courtesy of Drs. S. Halpain and I. Fischer), each at 1:1000, followed by biotinylated anti-rabbit IgG (1:100–1:200) and Texas Red-conjugated avidin (Vector). Neurons were defined as those cells with typical multipolar morphology and immunoreactivity for MAP-2.

Surgical samples. Both neuronally-committed and uncommitted subependymal progenitor cells were identified in 5 resected temporal lobe samples, using the cell type-selective markers Hu for neurons, and musashi for uncommitted progenitors (see below). The samples were each taken at surgery, and immersed immediately in 4% paraformaldehyde. From each, 12 µm cryostat sections of the forebrain were cut and mounted onto Vectabond-subbed slides. To identify Hu-immunoreactive SZ cells, MAb 16A11, which recognizes all 3 neuronal members of the Hu family (Marusich, 1992; Marusich, 1994, which are hereby incorporated by reference), was used as previously described, at 12.5 µg/ml, with avidin-biotin amplification, peroxidase-conjugated avidin detection, and diaminobenzidine (DAB)/$H_2O_2$ development (Barami, 1995, which is hereby incorporated by reference). Musashi was localized using rat monoclonal anti-mouse musashi IgG (Sakakibara, 1997; Sakakibara, 1996, which are hereby incorporated by reference), 1:500 overnight at 4° C., followed by biotinylated anti-rat IgG (1:100), and peroxidase-conjugated avidin-biotin (Vector), with DAB/$H_2O_2$ development.

$^3$H-thymidine Labeling and Autoradiography

The uptake of $^3$H-thymidine (0.2 µCi/plate, from 1 Ci/ml stock; 5 Ci/mM, Amersham) by antigenically-defined neurons was used as an index of antecedent precursor cell S-phase and division in vitro. Cultures were exposed to $^3$H-thymidine during their first 7 days in vitro, after which a complete media exchange removed residual isotope. After immunochemistry, the plates were air-dried, then autoradiographed as described (Kirschenbaum, 1994, which is hereby incorporated by reference). Briefly, Kodak NTB-3 emulsion was added to each petri dish for 3 min, then withdrawn by Pasteur pipette, leaving a remnant gel. After a week at 4° C. in the dark, the plates were developed with Kodak D-19, fixed, washed, covered with 50% glycerol in 0.1 M phosphate buffer, and observed with an Olympus IX70 microscope.

Calcium Imaging

To identify neurons physiologically, cells in selected plates were challenged with a depolarizing stimulus of 60 mM $K^+$, during which their cytosolic calcium levels were observed. Calcium imaging was performed using confocal microscopy of cultures loaded with fluo-3 acetometoxyester (fluo-3, Molecular Probes), as described previously (Kirschenbaum, 1994; Goldman, 1996a, which are hereby incorporated by reference). A Bio-Rad MRC600 confocal scanning microscope, equipped with an argon laser and coupled to a Nikon Diaphot 300 microscope, was used to image the fluo-3 signal. Each experiment was carried out at 25° C. in HBSS, with 60 mM $K^+$ exchanged for 60 mM $Na^+$ in the depolarizing solution.

These neurons were previously reported to display a mean calcium rise of >400% to 60 mM $K^+$ in vitro; this contrasted to an astrocytic calcium response of <20%, and undetectable oligodendroglial responses (Kirschenbaum, 1994, which is hereby incorporated by reference). On this basis, a 2-fold calcium increase to depolarization was required here for assigning neuronal identity.

Example 2

Neuronal Outgrowth Arose from Explants of the Adult Human SZ

In this series, 8 of 16 brains exhibited ependymoglial outgrowth. The other 8 exhibited no cellular outgrowth of any kind, and were deemed technical failures. The likelihood of successful outgrowth appeared to depend in part upon the transit time between the operating room and culture facility; the longest latencies to culture were associated with the worst explant survival and outgrowth. Among the 8 brains that exhibited outgrowth, cells with neuronal morphology and antigenicity were observed in outgrowths from 4 (a 6 month-old female, 27 year-old male, and 35 and 52 years old females). These cells were typically found upon a field of ependymal cells and astrocytes, as ovoid cell bodies with thin processes (FIG. 5). In 2 patients, the identity of neuron-like cells in the explant outgrowths was confirmed physiologically as well as antigenically (FIG. 5).

Example 3

Serial Exposure to FGF-2 and BDNF Promoted the Generation and Maintenance of Networks of New Neurons Among cultures raised sequentially in FGF-2 and BDNF, SZ outgrowths were noted that generated morphologically complex neuronal networks, some of which survived >2 months in culture (FIG. 5). In contrast, no plates raised in the absence of BDNF maintained viable neurons beyond a month in vitro, and none raised without both FGF2 and BDNF exhibited >10 neurons per explant. In selected FGF2/BDNF-treated surveillance cultures, the neuronal identity of cells was verified, both antigenically and physiologically. In one such case, 3 long-term cultures derived from one patient were subjected after 9 weeks in vitro to combined immunostaining for MAP-2 and autoradiography for $^3$H-thymidine. Among 55 MAP-2$^+$ neurons identified in these 3 cultures, 10 were double labeled as $^3$H-thymidine$^+$/MAP-2$^+$ (FIGS. 2 and 3). These data indicate division of mitotic progenitors during the first week in vitro, during the period of concurrent FGF-2 and $^3$H-thymidine exposure, though they do not necessarily indicate a direct causal relationship between FGF and neuronal mitogenesis.

Example 4

Neurons Generated from Adult SZ Explants in the Presence of FGF2/BDNF Developed Neuronal Calcium Responses to Depolarization To confirm the ability of these cells to respond in a neuronal fashion to depolarizing stimuli, selected cultures (n=6, derived from 2 brains) were loaded with the calcium indicator dye fluo-3, and exposed to 60 mM $K^+$ during confocal microscopy. Glial responses to depolarization were minimal under these culture conditions, as previously noted (Kirschenbaum, 1994, which is hereby incorporated by reference). In contrast, neuron-like cells verified as such displayed rapid, reversible, >100% elevations in cytosolic calcium in response to $K^+$, consistent with the activity of neuronal voltage-gated calcium channels (FIG. 5). The neuronal phenotype of these cells was then validated antigenically, by immunostaining for MAP-2 (FIG. 5).

Example 5
Neuronal Outgrowth was Noted on Rare Occasion from Neocortical Explants In cultures derived from two patients (a 27 years old male and 35 years old female), neuronal outgrowth was noted in cultures derived from the neocortex as well as the SZ. These cells survived up to 9 weeks in vitro, expressed MAP-2, and exhibited >100% increments in cell calcium to $K^+$-depolarization, consistent with their neuronal phenotype (FIG. 6). Some, like their SZ-derived counterparts, incorporated $^3$H-thymidine during the period of FGF-2 exposure. Long-term neuronal outgrowth from these cultures was limited to those that had been serially exposed to both FGF-2 and BDNF; untreated explants had no surviving neuronal outgrowth beyond a month in vitro. Depolarization-responsive MAP-2$^+$ neurons were also identified in dissociates from a second cortical sample, derived from a 35 years old female (these had not been exposed to thymidine in vitro).

In this series, over 800 neocortical explants were prepared from 8 different patients whose cultures exhibited at least glial outgrowth. Yet among these cortical explants, only 4, derived from 2 patients, exhibited neuronal outgrowth. Overall then, $\leq 0.5\%$ of cortical explants generated any neuronal outgrowth. Nonetheless, the observation of any MAP-2$^+$/$^3$H-thymidine$^+$, depolarization-responsive neurons in these outgrowths was remarkable, in that it argued for the existence of rare neuronal progenitors in the neocortical parenchyma.

Example 6
Immunostaining Revealed Cells Expressing the Early Neural Proteins Musashi and Hu in the Subependyma To identify neural progenitor cells and their daughters in vivo, the cells were immunostained for 2 RNA-binding proteins that characterize early neuronal phenotype, the musashi and Hu proteins. Musashi, a 39 kD RNA-binding protein initially described in Drosophila and Xenopus (Nakamura, 1994; Richter, 1990, which are hereby incorporated by reference), is expressed in development by mitotic neural progenitors, including CNS stem cells (Sakakibara, 1996, which is hereby incorporated by reference). In the adult rat brain, musashi expression is limited to progenitor cells of the lateral ventricular and olfactory subependyma. It is not expressed by mature neurons or oligodendrocytes, but is made by parenchymal astrocytes (Sakakibara, 1997, which is hereby incorporated by reference). In contrast, Hu comprises a family of 35–42 kD proteins (Szabo, 1991, which is hereby incorporated by reference), at least 3 of which, HuD, HuC and HelN1, are expressed selectively by neurons and their committed progenitors. In the CNS, Hu appears very early in neuronal ontogeny but is not expressed by cycling progenitors; in the SZ, it is an effective marker for neuronal daughter cells (Barami, 1995, which is hereby incorporated by reference).

For histological evaluation of progenitor phenotypes in the SZ, surgical samples of temporal horn ventricular epithelium were prepared as described from 5 patients (22 and 23 year-old males, and 9, 29, and 46 year-old females). In all 5, Hu$^+$ cells were found in the temporal ventricular subependyma. These cells were generally found in small clusters; typically several multicell clusters and scattered lone cells were observed per ventricular cross-section (FIG. 4). Among 18 sections of the temporal SZ, derived from 5 brain samples, an average of 10.1±0.8 (mean±SD) Hu$^+$ SZ cells/mm were found; this corresponded to a density of 78±22.6 Hu$^+$ cells per 1000 hematoxylin-defined subependymal cells (Table 1). Within the subjacent parenchyma, all neurons and some oligodendrocytes expressed Hu-IR; no astrocytic expression of Hu was ever noted.

TABLE 1

Distribution and Density of Antigenically-Defined Precursor (Musashi) and Daughter (Hu) Phenotypes in the Adult Human Temporal SZ A. Musashi$^+$ cells in the adult human temporal SZ (see FIG. 4A)

| Patient (age/sex) | Mean segment length (mm) | Total SZ cells | Musashi$^+$ cells/section | Musashi$^+$/mm | % Musashi$^+$ |
|---|---|---|---|---|---|
| 29/female | 11.014 ± 1.230 | 1123 ± 48 | 90 ± 9.1 | 8 ± 0.4 | 8 ± 0.6 |
| 22/male | 2.473 ± 0.969 | 361 ± 136 | 26 ± 7.5 | 11 ± 2.1 | 7.4 ± 1.3 |
| 9/female | 2.210 ± 0.040 | 411 ± 21 | 13 ± 2.1 | 6 ± 1.0 | 3.3 ± 0.5 |
| OVERALL | | | | 8 ± 2.4 | 6.2 ± 2.6% |

B. Hu$^+$ cells in the adult human temporal SZ (see FIG. 4B)

| Patient (age/sex) | Mean segment length (mm)$^{1,2}$ | SZ cells/section | Hu$^+$ cells/section | Hu$^+$/mm | % Hu$^+$ |
|---|---|---|---|---|---|
| 46/female | 3.913 ± 0.703 | 342 ± 23 | 44 ± 9.1 | 11 ± 1.1 | 11.1 ± 0.9% |
| 23/male | 2.286 ± 0.456 | 247 ± 45 | 21 ± 8.1 | 9 ± 2.0 | 7.2 ± 1.6% |
| 29/female | 9.409 ± 0.227 | 1088 ± 36 | 88 ± 4.5 | 9 ± 0.3 | 8.1 ± 0.5% |
| 22/male | 1.336 ± 0.158 | 173 ± 13 | 13 ± 1.5 | 10 ± 0.7 | 7.7 ± 0.3% |
| 9/female | 1.066 ± 0.256 | 238 ± 38 | 12 ± 2.5 | 11 ± 0.5 | 4.9 ± 0.4% |
| OVERALL | | | | 10 ± 0.8 | 7.8 ± 2.2% |

The density and distribution of musashi-immunoreactive (musashi$^+$) SZ cells was similar to that of Hu$^+$ SZ cells: an average of 8.4±2.4 musashi$^+$ cells per mm of ventricular surface were found, for a density of 62±26.0 musashi$^+$ cells per 1000 SZ cells (n=3 patients, 3 immunostained sections each) (FIG. 4; Table 1). Since double-labeling for both proteins was infrequent in this sample, of Hu$^+$ (7.8±2.3%) and musashi$^+$ (6.2±2.6%) cells together constituted <15% of temporal subependymal zone cells.

Neuronal outgrowth from explants of the adult temporal SZ were previously identified, and on that basis the existence of neuronal progenitors in mature humans was inferred (Barami, 1995, which is hereby incorporated by reference). However, neuronal outgrowth from these explants, raised in high-serum unsupplemented media, was relatively sparse (<10 neurons/productive explant), and their survival transient. The present invention shows that these neural precursor cells could be identified in situ, and that their production and sustenance of new neurons could be enhanced by neurotrophins identified as such in rodents. The sequential exposure of adult temporal SZ explants to FGF-2 and BDNF was associated with abundant and long-lasting neuronal outgrowth. In contrast, cultures grown in the absence of added FGF2 and BDNF exhibited neither neuronal outgrowth of this magnitude, nor survival of this duration. This was in accordance with the findings in cultures of the adult rat SZ, in which neuronal survival past the second week in vitro required BDNF addition (Kirschenbaum, 1995, which is hereby incorporated by reference).

In adult avian and rodent SZ cultures, those neurons that emigrate from the explants comprise the newly generated pool; virtually all incorporate $^3$H-thymidine in vivo, in the days before sacrifice, or shortly thereafter in culture (Goldman, 1992a; Lois, 1993; Kirschenbaum, 1995, which are hereby incorporated by reference). In adult human SZ cultures, the significant fraction of MAP-2$^+$ neurons that incorporated thymidine in vitro suggested that many if not all of the neurons in the explant outgrowths were similarly derived from mitotic progenitors.

Neuronal progenitors in the neocortical parenchyma were exceedingly rare. Nonetheless, the scarcity of these progenitors was perhaps not as surprising as was their very existence: Most previous studies have found that the source of neural precursors in both adult birds and mammals is the ventricular zone (Goldman, 1990; Lois, 1993; Morshead, 1994, which are hereby incorporated be reference), through which they are widely dispersed (Kirschenbaum, 1995; Weiss, 1996b; Nottebohm, 1985; Alvarez-Buylla, 1988, which are hereby incorporated by reference). Yet the neuronal precursors of the adult rodent brain have been reported to reside in parenchymal as well as ventricular sites (Richards, 1992; Palmer, 1995, which are hereby incorporated by reference), as have oligodendrocytic progenitors (Gensert, 1996, which is hereby incorporated by reference). Whether these adult cortical progenitors are homologous to their counterparts in either the developing cortex (Davis, 1994, which is hereby incorporated by reference) or adult SZ is unknown.

The nature of parenchymal neural precursor cells is unclear because of the epileptic pathology of these patients. In these samples, apparent cortical progenitors might have derived from cells in microheterotopic foci which were not apparent on routine pathologic examination. Interestingly, this opens the possibility that the heterotopic cell aggregations associated with several uncommon forms of refractory epilepsy, might include inappropriately situated neuronal precursors (Jay, 1994, which is hereby incorporated by reference). In particular, the nodular subependymal and subcortical white matter heterotopias, with their periventricular locales and granule cell predominance, might constitute reservoirs of subependymal cells with precursor potential (Dubeau, 1995; Huttenlocher, 1994; De Rosa, 1992; Raymond, 1994, which are hereby incorporated by reference). These heterotopic cell rests may be comprised of aberrant ventricular zone emigrants, that remain functionally quiescent, yet develop into neurons when presented a permissive in vitro environment. In this regard, it is intriguing that most patients with both nodular and laminar (band) heterotopias are female, and largely develop epilepsy during puberty (Raymond, 1994; Palmini, 1991b; Palmini, 1991a; Barkovich, 1994, which are hereby incorporated by reference). These include familial subependymal heterotopias, that appear to follow X-linked dominant inheritance (Huttenlocher, 1994, which is hereby incorporated by reference). In such cases, ectopic subependymal cells might conceivably persist as quiescent progenitors until the estrogenic stimulation associated with puberty, at which time they might assume neuronal function, with epileptogenic consequences.

In adult rodents, neurons and glial progenitors are abundant in the forebrain subependyma, in particular in the rostral dorsolateral aspect of the lateral ventricular system (Lois, 1993; Kirschenbaum, 1995; Morshead, 1994; Luskin, 1997, which are hereby incorporated by reference). While some of the neuronal progeny of these SZ cells die in situ (Morshead, 1992, which is hereby incorporated by reference), most appear to migrate rostrally to the olfactory bulb, in an adult manifestation of the rostral migratory stream first reported in the developing rodent brain (Altman, 1965; Frazier-Cierpial, 1989; Luskin, 1993b; Corotto, 1993; Lois, 1994, which are hereby incorporated by reference). In rodents, these new neurons migrate in chains within the subependymal milieu, without ever entering the brain parenchyma, in a novel form of neurophilic migration in the absence of radial guide fibers (Lois 1996; Doetsch, 1996, which are hereby incorporated by reference), In the present invention, these observations are extended to the human forebrain, where musashi and Hu expression was used to identify progenitors and their neuronally-committed daughters in the adult SZ. Significant subependymal populations of each phenotype were found. In the temporal horn of the lateral ventricle, musashi$^+$ cells were scattered about, singly and apparently stochastically. Hu$^+$ SZ cells were often found together in small aggregates, typically of no more than 3 cells. Whether these cells travel as chains more rostrally in the ventricular wall, and whether they are analogous to the new neurons of the rodent olfactory stream, remains to be seen.

Roughly 15% of the subependymal cells of the temporal horn expressed either musashi or Hu proteins. However, the virtual uniqueness of each sample with regards to disease state, sex, age, stereotaxic position and histological integrity made comparisons of Hu$^+$ and musashi$^+$ SZ cell distributions between samples difficult. It is similarly unclear whether these estimates are reflective of the distribution of musashi$^+$ and Hu$^+$ cells in other regions of the ventricular system: Analogy to the distribution of precursor cells in the adult rat, in which caudal regions of the ventricular system have the lowest numbers of progenitors (Kirschenbaum, 1995); Weiss, 1996b, which are hereby incorporated by reference) suggests that the area of human brain which was sampled might be expected to have a lower density of neuronal progenitor cells than more rostral regions, in particular that abutting the vestigial olfactory subependyma.

The presence of musashi and Hu$^+$ subependymal cells in the adult human epileptics, and their spatial colocalization with FGF2 and BDNF-responsive neuronal precursors, argues for the presence of neural precursors in the adult human subependyma. Some progenitors might also persist within the cortex itself. Though small in numbers, the ability of these cells to yield a profusion of new neurons in vitro suggests the promise of generating new neurons within the adult human brain.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

REFERENCES

Ahmed et al., "BDNF Enhances the Differentiation but not the Survival of CNS Stem Cell-Derived Neuronal Precursors," *J. Neurosci.*, 15:5765–5778 (1995).

Altman et al., "Autoradiographic and Histological Evidence of Postnatal Hippocampal Neurogenesis in Rats," *J. Comp. Neurol.*, 124:319–335 (1965).

Alvarez-Buylla et al., "Migration of Young Neurons in Adult Avian Brain," *Nature*, 335:353–354 (1988).

Alvarez-Buylla et al., "Neuronal Stem Cells in the Brain of Adult Vertebrates," *Stem Cells*, 13:263–272 (1995).

Anderson et al., "Molecular Probes for the Development and Plasticity of Neural Crest Derivatives," *Cell*, 42:649–662 (1985a).

Anderson et al., "Neurogenesis in Adult Vertebrate Spinal Cord In Situ and In Vitro: A New Model System," *Ann. N.Y. Acad. Sci.*, 457:213–233 (1985b).

Anderson et al., "A Bipotential Neuroendocrine Precursor whose Choice of Cell Fate is Determined by NGF and Glucocorticoids," *Cell*, 47:1079–1090 (1986).

Archer et al., "Myelination of the Canine Central Nervous System by Glial Cell Transplantation: A Model for Repati of Human Myelin Disease," *Nature Med.*, 3:54–59 (1997).

Armstrong et al., "Pre-Oligodendrocytes from Adult Humans CNS," *J. Neurosci.*, 12:1538–1547 (1992).

Austin, *Gene Ther.* 1 Suppl 1:S6–9 (1994)

Barami et al., "N-cadherin and Ng-CAM/8D9 are involved Serially in the Migration of Newly Generated Neurons into the Adult Songbird Brain," *Neuron*, 13:567–582 (1994).

Barami et al., "Hu Protein as an Early Marker of Neuronal Phenotypic Differentiation by Subependymal Zone Cells of the Adult Songbird Forebrain," *J. Neurobiol.*, 28:82–101 (1995).

Barkovich et al., "Band Heterotopia: Correlation of Outcome with Magnetic Resonance Imaging Parameters," *Ann. Neurol.*, 36:609–617 (1994).

Barres et al., "A Crucial Role for Neurotrophin-3 in Oligodendrocyte Development," *Nature*, 367:371–375 (1994).

Bartlett et al., "Immortalization of Mouse Neural Precursor Cells by the c-myc Oncogene [Published Erratum Appears in Proceedings of the National Academy of Sciences of the United States of America 86(3):1103 (1989)]" *Proc. Natl. Acad. Sci. U.S.A.*, 85:3255–3259 (1988).

Baudard, et al., *Hum. Gene Ther.*, 7:1309–22 (1996)

Bayer et al., "Neurons in the Rat Dentate Gyrus Granular Layer Substantially Increase During Juvenile and Adult Life," *Science*, 216:890–892 (1982).

Bernhardt et al., "Light and Electron Microscopic Studies of the Distribution of Microtubule-Associated Protein 2 in Rat Brain: A Difference Between Dendritic and Axonal Cytoskeletons," *J. Comp. Neurol.*, 226:203–221 (1984).

Bottenstein et al., "Grown of a Rat Neuroblastoma Cell Line in Serum-Free Supplemental Medium," *Proc. Natl. Acad. Sci. U.S.A.*, 76:514–517 (1979).

Boulder Committee, "Embryonic Vertebrate Central Nervous System: Revised Terminology," *Anat. Rec.*, 166:257–261 (1970).

Bronner-Fraser et al., "Cell Lineage Analysis Reveals Multipotency of Some Avian Neural Crest Cells," *Nature*, 335:161–164 (1988).

Brustle et al., "Neuronal Progenitors as Tools for Cell Replacement in the Nervous System," *Curr. Opin. Neurobiol.*, 6:688–695 (1996).

Collazo et al., "Vital Dye Labeling of xenopus laevis Trunk Neural Crest Reveals Multipotency and Novel Pathways of Migration," *Development*, 118:363–376 (1993).

Corotto et al., "Neurogenesis Persists in the Subependymal Layer of the Adult Mouse Brain," *Neurosci. Lett.*, 149:111–114 (1993).

Corti et al., "Intracerebral Tetracycline-Dependent Regulation of Gene Expression in Grafts of Neural Precursors," *Neuroreport*, 7:1655–1659 (1996).

Craig et al., "In Vivo Growth Factor Expansion of Endogenous Subependymal Neural Precursor Cell Populations in the Adult Mouse Brain," *J. Neurosci.*, 16:2649–2658 (1996).

Dahlstrand et al., "Characterization of the Human Nestin Gene Reveals a Close Evolutionary Relationship to Neurofilaments," *J Cell Sci*, 103:589–597 (1992).

Davis et al., "A Self-Renewing Multipotential Stem Cell in Embryonic Rat Cerebral Cortex," *Nature*, 372:263–266 (1994).

De Rosa et al., "Neuropathologic Findings in Surgically Treated Hemimegalencephaly: Immunohistochemical, Morphometric, and Ultrastructural Study," *Acta. Neuropathol. (Berl)*, 84:250–260 (1992).

DeHamer et al., "Genesis of Olfactory Receptor Neurons in Vitro: Regulation of Progenitor Cell Divisions by Fibroblast Growth Factors," *Neuron*, 13:1083–1097 (1994).

Deloulme et al., "Establishment of Pure Neuronal Cultures from Fetal Rat Spinal Cord and Proliferation of the Neuronal Precursor Cells in the Presence of Fibroblast Growth Factor," *J. Neurosci. Res*, 29:499–509 (1991).

DiCicco-Bloom et al., "Insulin Growth Factors Regulate the Mitotic Cycle in Cultured Rat Sympathetic Neuroblasts," *Proc. Natl. Acad. Sci. U.S.A.*, 85:4066–4070 (1988).

DiCicco-Bloom et al., "NT-3 Stimulates Sympathetic Neuroblast Proliferation by Promoting Precursor Survival," *Neuron*, 11:1101–111 (1993).

Doetsch et al., "Network of Tangential Pathways for Neuronal Migration in the Adult Mammalian Brain," *Proc. Natl. Acad. Sci. U.S.A.*, 93:14895–14900 (1996).

Drago et al., "Fibroblast Growth Factor-Mediated Proliferation of Central Nervous System Precursors Depends on Endogenous Production of Insulin-Like Growth Factor I, *Proc. Natl. Acad. Sci. U.S.A.*, 88:2199–2203 (1991).

Dubeau et al., "Periventricular and Subcortical Nodular Heterotopia. A Study of 33 Patients," *Brain*, 118(pt 5):1273–1287 (1995).

Eglitis, *Blood* 71:717–22 (1988)

Flax, et al., "Engraftable Human Neural Stem Cells Respond to Developmental Cues Replace Neurons, and Express Foreign Genes," *Nature Biotech.* 16:1033–39 (1998)

Flotte, et al., *Gene Ther.* 2:29–37 (1995)

Franklin et al., "Transplanted CG4 Cells (an Oligodendrocyte Progenitor Cell Line) Survive, Migrate, and Contribute to Repair of Areas of Demyelination in X-Irradiated and Damaged Spinal Cord but not in Normal Spinal Cord," *Exp. Neurol.*, 137:263–276 (1996).

Frazier-Cierpial et al., "Early Postnatal Cellular Proliferation and Survival in the Olfactory Bulb and Rostral Migratory Stream of Normal and Unilaterally Odor-Deprived Rats," *J. Comp. Neurol.*, 289:481–492 (1989).

Frederiksen et al., "Proliferation and Differentiation of Rat Neuroepithelial Precursor Cells in Vivo," *J. Neurosci.*, 8:1144–1151 (1988).

Freed et al., "Embryonic Dopamine Cell Implants as a Treatment for the Second Phase of Parkinson's Disease: Replacing Failed Nerve Terminals," *Adv. Neurol.*, 60:721–728 (1993).

Gage et al., "Morphological Response of Axotomized Septal Neurons to Nerve Growth Factor," *J. Comp. Neurol.*, 269:147–155 (1988).

Gage et al., "Gene Therapy in the CNS: Intracerebral Grafting of Genetically Modified Cells," *Prog. Brain Res.*, 86:205–217 (1990).

Gage et al., "Genetically Modified Cells: Applications for Intracerebral Grafting," *Trends Neurosci*, 14:328–333 (1991).

Gage et al., "Survival and Differentiation of Adult Neuronal Progenitor Cells Transplanted to the Adult Brain," *Proc. Natl. Acad. Sci. U.S.A.*, 92:11879–11883 (1995).

Gensburger et al., "Brain Basic Fibroblast Growth Factor Stimulates the Proliferation of Rat Neuronal Precursor Cells In Vitro," *FEBS Lett*, 217:1–5 (1987).

Gensert et al., "In Vivo Characterization of Endogenous Proliferating Cells in Adult Rat Subcortical White Matter," *Glia*, 17:39–51 (1996).

Gensert et al., "Endogenous Progenitors Remyelinate Demyelinated Axons in the Adult CNS," *Neuron*, 19:197–203 (1997).

Gloster et al., *J. Neuroscience*, 14:7319–30 (1994).

Golden et al., "Clones in the Chick Diencephalon Contain Multiple Cell Types and Siblings are Widely Dispersed," *Development*, 122:65–78 (1996).

Goldman et al., "Neuronal Production, Migration, and Differentiation in a Vocal Control nucleus of the Adult Female Canary Brain," *Proc. Natl. Acad. Sci. U.S.A.*, 80:2390–2394 (1983).

Goldman et al., "In Vitro Neurogenesis by Neuronal Precursor Cells Derived from the Adult Songbird Brain," *J. Neurosci.*, 12:2532–2541 (1992a).

Goldman et al., "Newly Generated Neurons of the Adult Songbird Brain become Functionally Active in Long-Term Culture," *Dev. Brain Res.*, 68:217–223 (1992b).

Goldman et al., "Migration of Newly Generated Neurons upon Ependymally Derived Radial Guide Cells in Explant Cultures of the Adult Songbird Forebrain," *Glia*, 8:150–160 (1993).

Goldman et al., "Transient Coupling of NgCAM Expression to NgCAM-Dependent Calcium-Signaling during Migration of New Neurons in the Adult Songbird Forebrain," *Mol. Cell. Neurosci.*, 7:29–45 (1996a).

Goldman et al., "Ventricular Zone Cells of the Adult Songbird Brain are Pluripotential for Neurons and Non-Neuronal Siblings, In Vitro and In Vivo," *J. Neurobiol.*, 30:505–520 (1996b).

Goldman et al., "Neuronal Precursor Cells of the Adult Rat Ventricular Zone Persist into Senescence, with no Change in Spatial Extent or BDNF Response," *J. Neurobiol.*, 32:554–566 (1997a).

Goldman, "Neuronal Development and Migration in Explant Cultures of the Adult Canary Forebrain," *J. Neurosci.*, 10:2931–2939 (1990).

Goldman, "Neuronal Precursor Cells and Neurogenesis in the Adult Forebrain," *Neuroscientist*, 1:338–350 (1995).

Goldman, "Comparative Strategies of Subependymal Neurogenesis in the Adult Forebrain. Isolation, Characterization and Utilization of CNS Stem Cells," *New York: Springer-Verlag*, 43–65 (1997).

Goldman, "Adult Neurogenesis: From Canaries to the Clinic," *J. Neurobiol.* 36:267–86 (1998)

Goldman and Luskin, "Strategies Utilized by Migrating Neurons of the Postnatal Vertebrate Forebrain," *Trends in Neurosci.* 21(3):107–14 (1998)

Gritti et al., "Multipotential Stem Cells from the Adult Mouse Brain Proliferate and Self-Renew in Response to Basic Fibroblast Growth Factor," *J. Neurosci.*, 16:1091–1100 (1996).

Grove et al., "Multiple Restricted Lineages in the Embryonic Rat Cerebral Cortex," *Development*, 117:553–561 (1993).

Groves et al., "Repair of Demyelinated Lesions by Transplantation of Purified O-2A Progenitor Cells," *Nature*, 362:453–455 (1993).

Halliday et al., "Generation and Migration of Cells in the Developing Striatum," *Neuron*, 9:15–26 (1992).

Holst et al., *J. Biol. Chem.*, 269:22245–52 (1994).

Hoshimaru et al., "Differentiation of the Immortalized Adult Neuronal Progenitor Cell Line HC2S2 into Neurons by Regulatable Suppression of the v-myc Oncogene," *Proc. Natl. Acad. Sci. U.S.A.*, 93:1518–1523 (1996).

Huttenlocher et al., "Periventricular Heterotopia and Epilepsy," *Neurology*, 44:51–55 (1994).

Jacobson, "*Developmental Neurobiology*," New York: Plenum Press (1991).

Jay et al., "Surgical Pathology of Epilepsy: A Review," *Pediatr. Pathol.*, 14:731–750 (1994).

Kaplan et al., "Neurogenesis in the Adult Rat: Electron Microscopic Analysis of Light Radioautographs," *Science*, 197:1092–1094 (1977).

Kaplan et al., "Population Dynamics of Adult-Formed Granule Neurons of the Rat Olfactory Bulb," *J. Comp. Neurol.*, 239:117–125 (1985).

Kilpatrick et al., "Cloning and Growth of Multipotential Neural Precursors: Requirements for Proliferation and Differentiation," *Neuron*, 10:255–265 (1993).

Kilpatrick et al., "Cloned Multipotential Precursors from the Mouse Cerebrum Require FGF-2, Whereas Glial Restricted Precursors are Stimulated with Either FGF-2 or EGF," *J. Neurosci.*, 15:3653–3661 (1995).

Kirschenbaum et al., "In Vitro Neuronal Production and Differentiation by Precursor Cells Derived from the Adult Human Forebrain," *Cereb. Cortex*, 4:576–589 (1994).

Kirschenbaum et al., "Brain-Derived Neurotrophic Factor Promotes the Survival of Neurons Arising from the Adult Rat Forebrain Subependymal Zone," *Proc. Natl. Acad. Sci. U.S.A.* 92:210–214 (1995).

Kitchens et al., "FGF and EGF are Mitogens for Immortalized Neural Progenitors," *J. Neurobiol.*, 25:797–807 (1994).

Kornack et al., "Radial and Horizontal Deployment of Clonally Related Cells in the Primate Neocortex: Relationship to Distinct Mitotic Lineages," *Neuron*, 15:311–321 (1995).

Korr, "Proliferation of Different Cell Types in the Brain," *Adv. Anat. Embryol. Cell. Biol.*, 61:1–72 (1980).

Kuhn et al., "Neurogenesis in the Dentate Gyrus of the Adult Rat: Age-Related Decrease of Neuronal Progenitor Proliferation," *J. Neurosci.*, 16:2027–2033 (1996).

Lacorazza, "Expression of Human β-hexosaminidase A-Subunit Gene (the Gene Defect of Tay-Sachs Disease) in Mouse Brains upon Engraftment of Transduced Progenitor Cells," *Nature Med.*, 2:424–429 (1996).

LaVail et al., "The Development of the Chick Optic Tectum: II-Autoradiographic Studies," *Brain Res.*, 28:421–441 (1971).

Lendahl et al., "CNS Stem Cells Express a New Class of Intermediate Filament Protein," *Cell*, 60:585–595 (1990a).

Lendahl et al., "The Use of Cell Lines in Neurobiology," *Trends Neurosci.*, 13:132–137 (1990b).

Leonard et al., "A Documentation of an Age-Related Increase in Neuronal and Axonal Numbers in the Stingray," *J. Comp. Neurol.*, 179:13–22 (1978).

Lillien et al., "Type-2 Astrocyte Development in Rat Brain Cultures is Initiated by a CNTF-Like Protein Produced by Type-1 Astrocytes," *Neuron*, 1:485–494 (1988).

Lois et al., "Proliferating Subventricular Zone Cells in the Adult Mammalian Forebrain can Differentiate into Neurons and Glia," *Proc. Natl. Acad. Sci. U.S.A.*, 90:2074–2077 (1993).

Lois et al., "Long-Distance Neuronal Migration in the Adult Mammalian Brain," *Science*, 264:1145–1148 (1994).

Lois et al., "Chain Migration of Neuronal Precursors," *Science*, 271:978–981 (1996).

Lopez-Garcia et al., "Delayed Postnatal Neurogenesis in the Cerebral Cortex of Lizards," *Brain Res.*, 471:167–174 (1988).

Lu et al., "A Paradigm for Distinguishing the Roles of Mitogenesis and Trophism in Neuronal Precursor Proliferation," *Brain Res. Dev. Brain Res.*, 94:31–36 (1996).

Luskin et al., "Cell Lineage in the Cerebral Cortex of the Mouse Studied In Vivo and In Vitro with a Recombinant Retrovirus," *Neuron*, 1:635–647 (1988).

Luskin et al., "Neurons, Astrocytes, and Oligodendrocytes of the Rat Cerebral Cortex Originate from Separate Progenitor Cells: An Ultrastructural Analysis of Clonally Related Cells," *J. Neurosci.*, 13:1730–1750 (1993a).

Luskin, "Restricted Proliferation and Migration of Postnatally Generated Neurons Derived from the Forebrain Subventricular Zone," *Neuron*, 11:173–189 (1993b).

Luskin et al., "Neuronal Progenitor Cells Derived from the Anterior Subventricular Zone of the Neonatal Rat Forebrain Continue to Proliferate In Vitro and Express Neuronal Phenotype," *Mol. Cell. Neurosci.*, 8:351–366 (1997).

Martinez-Serrano et al., "CNS-derived Neural Progenitor Cells for Gene Transfer of Nerve Growth Factor to the Adult Rat Brain: Complete Rescue of Axotomized Cholinergic Neurons after Transplantation into the Septum," *J. Neurosci.*, 15:5668–5680 (1995).

Marusich et al., "Identification of Early Neurogenic Cells in the Neural Crest Lineage," *Dev. Biol.*, 149:295–306 (1992).

Marusich et al., "Hu Neuronal Proteins are Expressed in Proliferating Neurogenic Cells," *J. Neurobiol.*, 25:143–155 (1994).

McKinnon et al., "Distinct Effects of bFGF and PDGF on Oligodendrocyte Progenitor Cells," *Glia*, 7:245–254 (1993).

Mehler et al., "Cytokine Regulation of Neuronal Differentiation of Hippocampal Progenitor Cells, *Nature*, 362:62–65 (1993).

Moretto et al., "Co-Expression of mRNA for Neurotrophic Factors in Human Neurons and Glial Cells in Culture," *J. Neuropathol. Exp. Neurol.*, 53:78–85 (1994).

Morshead et al., "Postmitotic Death is the Fate of Constitutively Proliferating Cells in the Subependymal Layer of the Adult Mouse Brain," *J. Neurosci.*, 12:249–256 (1992).

Morshead et al., "Neural Stem Cells in the Adult Mammalian Forebrain: A Relatively Quiescent Subpopulation of Subependymal Cells," *Neuron*, 13:1071–1082 (1994).

Murphy et al., "Fibroblast Growth Factor Stimulates the Proliferation and Differentiation of Neural Precursor Cells In Vitro," *J. Neurosci. Res*, 25:463–475 (1990).

Murphy et al., "Generation of Sensory Neurons is Stimulated by Leukemia Inhibitory Factor," *Proc. Natl. Acad. Sci. U.S.A.*, 88:3498–3501 (1991).

Murphy et al., "FGF2 Regulates Proliferation of Neural Crest Cells, with Subsequent Neuronal Differentiation Regulated by LIF or Related Factors," *Development*, 120:3519–3528 (1994).

Nakamura et al., "A Neural RNA-Binding Protein Required for Drosophila Adult External Sensory Organ Development," *Neuron*, 13:67–81 (1994).

Nottebohm, "Neuronal Replacement in Adulthood," *Ann. N.Y. Acad. Sci.*, 457:143–161 (1985).

Oldfield et al., "Gene Therapy for the Treatment of Brain Tumors using Intra-Tumoral Transduction with the Thymidine Kniase Gene and Intravenous Ganciclovir," *Hum. Gene Ther.*, 4:39–69 (1993).

Palmer et al., "FGF-2 Responsive Neuronal Progenitors Reside in Proliferative and Quiescent Regions of the Adult Rodent Brain," *Mol. Cell. Neurosci.*, 6:474–486 (1995).

Palmini et al., "Diffuse Cortical Dysplasia, or the "Double Cortex" Syndrome: The Clinical and Epileptic Spectrum in 10 Patients," *Neurology*, 41:1656–1662 (1991a).

Palmini et al., "Neuronal Migration Disorders: A Contribution of Modem Neuroimaging to the Etiologic Diagnosis of Epilepsy," *Can. J. Neurol. Sci.*, 18(suppl 4):580–587 (1991b).

Pincus et al., "Vasoactive Intestinal Peptide Regulates Mitosis, Differentiation and Survival of Cultured Sympathetic Neuroblasts," *Nature*, 343:564–567 (1990).

Pincus et al., "Fibroblast Growth Factor-2/Brain-Derived Neurotrophic Factor-Associated Maturation Of New Neurons Generated From Adult Human Subependymal Cells," *Ann. Neurol.*, 43(5):576–85 (1998).

Price et al., "Lineage Analysis in the Vertebrate Nervous System by Retrovirus-Mediated Gene Transfer," *Proc. Natl. Acad. Sci. U.S.A.*, 84:156–160 (1987).

Qian et al., "FGF2 Concentration Regulates the Generation of Neurons and Glia from Multipotent Cortical Stem Cells," *Neuron*, 18:81–93 (1997).

Raff et al., "A Glial Progenitor Cell that Develops In Vitro into an Astrocyte or an Oligodendrocyte Depending on Culture Medium," *Nature*, 303:390–396 (1983).

Raff et al., "Platelet-Derived Growth Factor from Astrocytes Drives the Clock that Times Oligodendrocyte Development in Culture," *Nature*, 333:562–565 (1988).

Rakic, "Guidance of Neurons Migrating to the Fetal Monkey Neocortex," *Brain Res.*, 33:471–476 (1971).

Rakic, "Neurons in Rhesus Monkey Visual Cortex: Systematic Relation Between the Time of Origin and Eventual Disposition," *Science*, 183:425–427 (1974).

Ray et al., "Proliferation, Differentiation, and Long-Term Culture of Primary Hippocampal Neurons," *Proc. Natl. Acad. Sci. U.S.A.*, 90:3602–3606 (1993).

Ray et al., "Spinal Cord Neuroblasts Proliferate in Response to Basic Fibroblast Growth Factor," *J. Neurosci.*, 14:3548–3564 (1994).

Raymond et al., "Association of Hippocampal Sclerosis with Cortical Dysgenesis in Patients with Epilepsy," *Neurology*, 44:1841–1845 (1994).

Renfranz et al., "Region-Specific Differentiation of the Hippocampal Stem Cell Line HiB5 upon Implantation into the Developing Mammalian Brain," *Cell*, 66:713–729 (1991).

Reynolds et al., "A Multipotent EGF-Responsive Striatal Embryonic Progenitor Cell Produces Neurons and Astrocytes," *J. Neurosci.*, 12:4565–4574 (1992a).

Reynolds et al., "Generation of Neurons and Astrocytes from Isolated Cells of the Adult Mammalian Central Nervous System," *Science*, 255:1707–1710 (1992b).

Reynolds et al., "Clonal and Population Analyses Demonstrate that an EGF-Responsive Mammalian Embryonic CNS Precursor is a Stem Cell," *Dev. Biol.*, 175:1–13 (1996).

Richards et al., "De Novo Generation of Neuronal Cells from the Adult Mouse Brain," *Proc. Natl. Acad. Sci. U.S.A.*, 89:8591–8595 (1992).

Richter et al., "A Developmentally Regulated, Nervous System Specific Gene in Xenopus Encodes a Putative RNA-Binding Protein," *New Biologist*, 2:556–565 (1990).

Ryder et al., "Establishment and Characterization of Multipotent Neural Cell Lines using Retrovirus Vector-Mediated Oncogene Transfer," *J. Neurobiol.*, 21:356–375 (1990).

Sabate et al., "Transplantation to the Rat Brain of Human Neural Progenitors that were Genetically Modified using Adenoviruses," *Nat. Genet.*, 9:256–260 (1995).

Sakakibara et al., "Mouse-Musashi-1, a Neural RNA-Binding Protein Highly Enriched in the Mammalian CNS Stem Cell," *Dev. Biol.*, 176:230–242 (1996).

Sakakibara et al., "Expression of Neural RNA-Binding Proteins in the Postnatal CNS: Implications of Their Roles in Neuronal and Glial Cell Development," *J. Neurosci.*, 17:8300–8312 (1997).

Santa-Olalla et al., "Epidermal Growth Factor (EGF), Transforming Growth Factor-Alpha (TGF-alpha), and Basic Fibroblast Growth Factor (bFGF) Differentially Influence Neural Precursor Cells of Mouse Embryonic Mesencephalon," *J. Neurosci. Res.*, 42:172–183 (1995).

Scolding et al., "A Proliferative Adult Human Oligodendrocyte Progenitor," *Neuroreport*, 6:441–445 (1995).

Shah et al., "Glial Growth Factor Restricts Mammalian Neural Crest Stem Cells to a Glial Fate," *Cell*, 77:349–360 (1994).

Shihabuddin et al., "The Adult CNS Retains the Potential to Direct Region-Specific Differentiation of a Transplanted Neuronal Precursor Cell Line," *J. Neurosci.*, 15:6666–6678 (1995).

Shihabuddin et al., "Induction of Mature Neuronal Properties in Immortalized Neuronal Precursor Cells Following Grafting into the Neonatal CNS," *J. Neurocytol.*, 25:101–111 (1996).

Sidman et al., "Neuronal Migration, with Special Reference to Developing Human Brain: A Review," *Brain Res.*, 62:1–35 (1973).

Sieber-Blum, "Role of the Neurotrophic Factors BDNF and NGF in the Commitment of Pluripotent Neural Crest Cells," *Neuron*, 6:949–955 (1991).

Snyder et al., "Multipotent Neural Cell Lines can Engraft and Participate in Development of Mouse Cerebellum," *Cell*, 68:33–51 (1992).

Snyder et al., "Neural Progenitor Cell Engraftment Corrects Lysosomal Storage Throughout the MPS VII Mouse Brain," *Nature*, 374:367–370 (1995).

Snyder et al., "Multipotential Neural Precursors can Differentiate Tower Replacement of Neurons Undergoing Targeted Apoptotic Degeneration in Adult Mouse Neocortex," *Proc. Natl. Acad. Sci. U.S.A.*, 94:11663–11668 (1997).

Spencer et al., "Unilateral Transplantation of Human Fetal Mesencephalic Tissue into the Caudate Nucleus of Patients with Parkinson's Disease," *New Eng. J. Med.*, 327:1541–1548 (1992).

Stemple et al., "Isolation of a Stem Cell for Neurons and Glia from the Mammalian Neural Crest," *Cell*, 71:973–985 (1992).

Sturrock, "Changes in Cell Number in the Central Canal Ependyma and in the Dorsal Grey Matter of the Rabbit Thoracic Spinal Cord During Fetal Development," *J. Anat.*, 135:635–647 (1982).

Suhonen et al., "Differentiation of Adult Hippocampus-Derived Progenitors into Olfactory Neurons In Vivo," *Nature*, 383:624–627 (1996).

Szabo et al., "HuD, a Paraneoplastic Encephalomyelitis Antigen, Contains RNA Binding Domains and is Homologous to Elav and Sex-Lethal," *Cell*, 67:325–333 (1991).

Takebayashi et al., *J. Biol. Chem.*, 270:1342–49 (1995).

Temple et al., "Differentiation of a Bipotential Glial Progenitor Cell in a Single Cell Microculture," *Nature*, 313:223–225 (1985).

Temple et al., "Isolated Rat Cortical Progenitor Cells are Maintained in Division In Vitro by Membrane-Associated Factors," *Development*, 120:999–1008 (1994).

Turner et al., "A Common Progenitor for Neurons and Glia Persists in Rat Retina Late in Development," *Nature*, 328:131–136 (1987).

Vescovi et al., "bGFG regulates the Proliferative Fate of Unipotent (Neuronal) and Bipotent (Neuronal/

Astroglial) EGF-Generated CNS Progenitor Cells," *Neuron*, 11:951–966 (1993).

Wang et al., "Isolation of Forebrain Neuronal Precursors by Sorting Embryonic Forebrain Transfected with GFP Regulated by the $T_{21}$ Tubulin Promoter," *Nature Biotech.*, 16:196–201 (1998).

Waxman et al., "Generation of Electromotor Neurons in Stenarchus Albifrons: Differences Between Normally Growing and Regenerating Spinal Cord," *Dev. Biol.*, 112:338–344 (1985).

Weiss et al., "Is There a Neural Stem Cell in the Mammalian Forebrain?," *Trends Neurosci.*, 19:387–393 (1996a).

Weiss et al., "Multipotent CNS Stem Cells are Present in the Adult Mammalian Spinal Cord and Ventricular Neuroaxis," *J. Neurosci.*, 16:7599–7609 (1996b).

Wetts et al., "Multipotent Precursors can give Rise to All Major Cell Types of the Frog Retina," *Science*, 239:1142–1145 (1988).

Widner et al., "Bilateral Fetal Mesencephalic Grafting in Two Patients with Parkinsonism Induced by 1-methyl-4-phenyl-1,2,3,6-tetrahydropyridine (MPTP)," *New Eng. J. Med.*, 327:1556–1563 (1992).

Williams et al., "Continuous Infusion of Nerve Growth Factor Prevents Basal Forebrain Neuronal Death after Fimbria Fornix Transection," *Proc. Natl. Acad. Sci. U.S.A.*, 83:9231–9235 (1986).

Williams et al., "The Generation of Neurons and Oligodendrocytes from a Common Precursor Cell," *Neuron*, 7:685–693 (1991).

Williams et al., "Evidence for Multiple Precursor Cell Types in the Embryonic Rat Cerebral Cortex," *Neuron*, 14:1181–1188 (1995).

Wolswijk et al., "Cooperation Between PDGF and FGF Converts Slowly Dividing O-2A Adult Progenitor Cells to Rapidly Dividing Cells with Characteristics of O-2A Perinatal Progenitor Cells," *J. Cell. Biol.*, 118:889–900 (1992).

Zeitlin, et al., *Gene Ther.* 2:623–31 (1995)

Zigova, et al., "Intraventricular Administration of BDNF Increases the Number of Newly Generated Neurons in the Adult Olfactory Bulb," *Molec. And Cell. Neurosci.* 11:234–45 (1998)

What is claimed is:

1. Human neuronal progenitor cells isolated from non-embryonal human brain tissue and committed to formation of neurons, wherein the neurons express a Hu protein.

2. The human neuronal progenitor cells according to claim 1, wherein the progenitor cells are isolated from the brain's ependyma and subependyma.

3. The human neuronal progenitor cells according to claim 1, wherein the Hu protein is selected from the group consisting of HuD, HuC, and HelN1.

4. A method of propagating neurons and differentiating from neuronal progenitor cells derived from human brain tissue and committed to formation of neurons comprising:

applying serially FGF2 and BDNF to the neuronal progenitor cells in vitro under conditions effective to propagate neurons and to differentiate neuronal progenitor cells derived from human brain tissue and committed to formation of neurons.

5. The method according to claim 4 further comprising:

applying IGF1 to the neuronal progenitor cells in vitro.

6. The method according to claim 4, wherein the brain tissue is fetal brain tissue.

7. The method according to claim 4, wherein the brain tissue is juvenile or adult brain tissue.

8. The method according to claim 4, wherein the brain tissue contains subependymal, subcortical, or cortical progenitors.

9. A method of enhancing survival and function of human neuronal progenitor cells which are committed to formation of neurons and cells descending from the neuronal progenitor cells comprising:

transducing the human neuronal progenitor cells with a gene encoding an autocrine neurotrophin or an adhesion molecule in vitro under conditions effective to enhance survival and function of human neuronal progenitor cells which are committed to formation of neurons and cells descending from the neuronal progenitor cells.

10. The method according to claim 9, wherein the gene encodes an autocrine neurotrophin which is selected from the group consisting of FGF2, BDNF, and IGF1.

11. A neuronal progenitor cell produced by the method of claim 9.

12. The neuronal progenitor cell according to claim 11, wherein the autocrine neurotrophin is selected from the group consisting of FGF2, BDNF, and IGF1.

13. The method according to claim 9, wherein the gene encodes an adhesion molecule.

14. The method according to claim 13, wherein the adhesion molecule is selected from the group consisting of N-CAM, NgCAM, and a member of the integrin-family of proteins.

15. A neuronal progenitor cell provided by the method of claim 13.

16. The neuronal progenitor cell according to claim 15, wherein the adhesion molecule is selected from the group consisting of N-CAM, NgCAM, and a member of the integrin-family of proteins.

17. A method of detecting human neuronal progenitor cells committed to formation of neurons comprising:

providing an antibody directed against a protein which is preferentially associated with human neuronal progenitor cells when compared to other cell types, wherein the human neuronal progenitor cells are committed to formation of neurons;

contacting cells with the antibody; and detecting cells which bind to the antibody.

18. The method according to claim 17, wherein the protein is a Hu protein.

19. The method according to claim 18, wherein the Hu protein is selected from the group consisting of HuD, HuC, and HelN1.

20. The method according to claim 17, wherein the protein is a musashi protein.

21. A method of separating human, non-embryonal neural or neuronal progenitor cells from a mixed population of cells from human brain tissue, said method comprising:

selecting a promoter which functions only in human postnatal neural and neuronal progenitor cells;

introducing a nucleic acid molecule encoding a fluorescent protein under control of said promoter into the mixed population of cells;

allowing the non-embryonal neural or neuronal progenitor cells thereof to express the fluorescent protein; and separating the fluorescent cells from the mixed population of cells, wherein said separated cells are said neural or neuronal progenitor cells.

22. A method according to claim 21, wherein said introducing is selected from the group consisting of viral mediated transformation of the mixed population of cells, electroporation, and liposomal mediated transformation of the mixed population of cells.

23. A method according to claim 21, wherein said separating comprises fluorescence activated cell sorting.

24. A method according to claim 21, wherein the promoter is selected from the group consisting of a Hu promoter, a Musashi promoter, and a Nestin enhancer-promoter.

25. A method of detecting neural progenitor cells comprising:

proveiding an antibody directed against a musashi protein which is preferentially associated with neural progenitor cells when compared to other cell types;

contacting cells with the antibody; and detecting cells which bind to the antibody.

* * * * *